(12) United States Patent
Hampson et al.

(10) Patent No.: US 6,630,507 B1
(45) Date of Patent: Oct. 7, 2003

(54) CANNABINOIDS AS ANTIOXIDANTS AND NEUROPROTECTANTS

(75) Inventors: Aidan J. Hampson, Irvine, CA (US); Julius Axelrod, Rockville, MD (US); Maurizio Grimaldi, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/674,028

(22) PCT Filed: Apr. 21, 1999

(86) PCT No.: PCT/US99/08769
§ 371 (c)(1),
(2), (4) Date: Feb. 2, 2001

(87) PCT Pub. No.: WO99/53917
PCT Pub. Date: Oct. 28, 1999

Related U.S. Application Data

(60) Provisional application No. 60/082,589, filed on Apr. 21, 1998, and provisional application No. 60/095,993, filed on Aug. 10, 1998.

(51) Int. Cl.⁷ .............................................. A61K 31/35
(52) U.S. Cl. ....................................................... 514/454
(58) Field of Search ........................................ 514/454

(56) References Cited

U.S. PATENT DOCUMENTS

| | | | |
|---|---|---|---|
| 2,304,669 A | 12/1942 | Adams | 568/743 |
| 4,876,276 A | 10/1989 | Mechoulam et al. | 514/454 |
| 5,227,537 A | 7/1993 | Stoss et al. | 568/811 |
| 5,284,867 A | 2/1994 | Kloog et al. | 514/454 |
| 5,434,295 A | 7/1995 | Mechoulam et al. | 560/141 |
| 5,462,946 A | 10/1995 | Mitchell et al. | 514/315 |
| 5,512,270 A | 4/1996 | Ghio et al. | 424/45 |
| 5,521,215 A | 5/1996 | Mechoulam et al. | 514/454 |
| 5,538,993 A | 7/1996 | Mechoulam et al. | 514/454 |
| 5,635,530 A | 6/1997 | Mechoulam et al. | 514/454 |
| 5,696,109 A | 12/1997 | Malfroy-Camine et al. | 514/185 |
| 6,410,588 B1 | 6/2002 | Feldmann et al. | 514/454 |

FOREIGN PATENT DOCUMENTS

| | | |
|---|---|---|
| EP | 427518 A1 | 5/1991 |
| EP | 576357 A1 | 12/1993 |
| EP | 656354 A1 | 6/1995 |
| EP | 658546 A1 | 6/1995 |
| WO | WO9305031 A1 | 3/1993 |
| WO | WO9412667 A1 | 6/1994 |
| WO | WO9612485 A1 | 5/1996 |
| WO | WO9618600 A1 | 6/1996 |
| WO | WO9719063 A1 | 5/1997 |
| WO | 99/53917 | * 10/1999 |

OTHER PUBLICATIONS

Windholz et al., The Merck Index, Tenth Edition (1983) p. 241, abstract No. 1723.*
Mechoulam et al., "A Total Synthesis of dl–Δ¹–Tetrahydrocannabinol, the Active Constituent of Hashish¹," *Journal of the American Chemical Society*, 87:14:3273–3275 (1965).
Mechoulam et al., "Chemical Basis of Hashish Activity," *Science*, 18:611–612 (1970).
Ottersen et al., "The Crystal and Molecular Structure of Cannabidiol," *Acta Chem. Scand. B 31*, 9:807–812 (1977).
Cunha et al., "Chronic Administration of Cannabidiol to Healthy Volunteers and Epileptic Patients¹," *Pharmacology*, 21:175–185 (1980).
Consroe et al., "Acute and Chronic Antiepileptic Drug Effects in Audiogenic Seizure–Susceptible Rats," *Experimental Neurology*, Academic Press Inc., 70:626–637 (1980).
Turkanis et al., "Electrophysiologic Properties of the Cannabinoids," *J. Clin. Pharmacol.*, 21:449S–463S (1981).
Carlini et al., "Hypnotic and Antielpileptic Effects of Cannabidiol," *J. Clin. Pharmacol.*, 21:417S–427S (1981).
Karler et al., "The Cannabinoids as Potential Antiepileptics," *J. Clin. Pharmacol.*, 21:437S–448S (1981).
Consroe et al., "Antiepileptic Potential of Cannabidiol Analgos," *J. Clin. Pharmacol.*, 21:428S–436S (1981).

(List continued on next page.)

Primary Examiner—Kevin E. Weddington
(74) Attorney, Agent, or Firm—Klarquist Sparkman, LLP

(57) ABSTRACT

Cannabinoids have been found to have antioxidant properties, unrelated to NMDA receptor antagonism. This new found property makes cannabinoids useful in the treatment and prophylaxis of wide variety of oxidation associated diseases, such as ischemic, age-related, inflammatory and autoimmune diseases. The cannabinoids are found to have particular application as neuroprotectants, for example in limiting neurological damage following ischemic insults, such as stroke and trauma, or in the treatment of neurodegenerative diseases, such as Alzheimer's disease, Parkinson's disease and HIV dementia. Nonpsychoactive cannabinoids, such as cannabidoil, are particularly advantageous to use because they avoid toxicity that is encountered with psychoactive cannabinoids at high doses useful in the method of the present invention. A particular disclosed class of cannabinoids useful as neuroprotective antioxidants is formula (I) wherein the R group is independently selected from the group consisting of H, $CH_3$, and $COCH_3$.

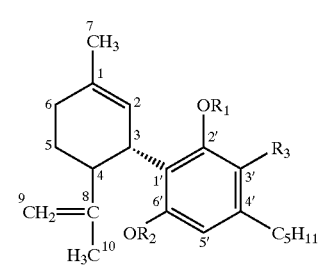

26 Claims, 7 Drawing Sheets

OTHER PUBLICATIONS

Colasanti et al., "Ocular Hypotension, Ocular Toxicity,a nd Neurotoxicity in Response to Marihuana Extract and Cannabidiol," *Gen Pharm.*, Pergamon Press Ltd., 15(6):479–484 (1984).

Colasanti et al., "Intraocular Pressure, Ocular Toxicity and Neurotoxicity after Administration of Cannabinol or Cannabigerol," *Exp. Eye Res.*, Academic Press Inc., 39:251–259 (1984).

Volfe et al., "Cannabinoids Block Release of Serotonin from Platelets Induced by Plasma frm Migraine Patients," *Int. J. Clin. Pharm. Res.*, Bioscience Ediprint Inc., 4:243–246 (1985).

Agurell et al., "Pharmacokinetics and Metabolism of $\Delta^1$–Tetrahydrocannabinol and Other Cannabinoids with Emphasis on Man*," *Pharmacological Reviews*, 38(1):21–43 (1986).

Karler et al., "Different Cannabinoids Exhibit Different Pharmacological and Toxicological Properties,"*NIDA Res. Monogr.*, 79:96–107 (1987).

Samara et al., "Pharmacokinetics of Cannabidiol in Dogs," *Drug Metabolism and Disposition*, 16(3):469–472 (1988).

Choi, "Glutamate Neurotoxicity and Diseases of the Nervous System," *Neuron*, Cell Press, 1:623–634 (1988).

Eshhar et al., "Neuroprotective and Antioxidant Activities of HU–211, A Novel NMDA Receptor Antagonist," *European Journal of Pharmacology*, 283:19–29 (1995).

Skaper et al., "The ALIAmide Palmitoylethanolamide and Cannabinoids, but not Anandamide, are Protective in a Delayed Postglutamate Paradigm of Excitotoxic Death in Cerebellar Granule Neurons," *Neurobiology*, Proc. Natl. Acad. Sci. USA, 93:3984–3989 (1996).

Alonso et al., "Simple Synthesis of 5–Substituted Resorcinols: A Revisited Family of Interesting Bioactive Molecules," *J. Org. Chem.*, American Chemical Society, 62(2):417–421 (1997).

Combes et al. "A Simple Synthesis of the Natural 2,5–Dialkylresorcinol Free Radical Scavenger Antioxidant: Resorstation," *Synthetic Communications*, Marcel Dekker, Inc., 27(21):3769–3778 (1997).

Shohami et al., "Oxidative Stress in Closed–Head Injury: Brain Antioxidant Capacity as an Indicator of Functional Outcome," *Journal of Cerebral Blood Flow and Metabolism*, Lippincott–Raven Publishers, 17(10):1007–1019 (1997).

Zurier et al., "Dimethylheptyl–THC–11 OIC Acid," *Arthritis & Rheumatism*, 41(1):163–170 (1998).

Hampson et al., "Dual Effects of Anandamide on NMDA Receptor–Mediated Responses and Neurotransmission," *Journal of Neurochemistry*, Lippincott–Raven Publishers, 70(2):671–676 (1998).

Hampson et al., "Cannabidiol and (–)$\Delta^9$–tetrahydrocannabiono are Neuroprotective Antioxidants," *Medical Sciences*, Proc. Natl. Acad. Sci. USA, 8268–8273 (1998).

* cited by examiner

CANNABINOIDS AS ANTIOXIDANTS AND NEUROPROTECTANTS

This application is a 371 of PCT/US99/08769 filed Apr. 21, 1999, which claims benefit of No. 60/082,589 filed Apr. 21, 1998, which claims benefit of No. 60/095,993 filed Aug. 10, 1998.

FIELD OF THE INVENTION

The present invention concerns pharmaceutical compounds and compositions that are useful as tissue protectants, such as neuroprotectants and cardioprotectants. The compounds and compositions may be used, for example, in the treatment of acute ischemic neurological insults or chronic neurodegenerative diseases.

BACKGROUND OF THE INVENTION

Permanent injury to the central nervous system (CNS) occurs in a variety of medical conditions, and has been the subject of intense scientific scrutiny in recent years. It is known that the brain has high metabolic requirements, and that it can suffer permanent neurologic damage if deprived of sufficient oxygen (hypoxia) for even a few minutes. In the absence of oxygen (anoxia), mitochondrial production of ATP cannot meet the metabolic requirements of the brain, and tissue damage occurs. This process is exacerbated by neuronal release of the neurotransmitter glutamate, which stimulates NMDA (N-methyl-D-aspartate), AMPA (α-amino-3-hydroxy-5-methyl-4-isoxazole propionate) and kainate receptors. Activation of these receptors initiates calcium influx into the neurons, and production of reactive oxygen species, which are potent toxins that damage important cellular structures such as membranes, DNA and enzymes.

The brain has many redundant blood supplies, which means that its tissue is seldom completely deprived of oxygen, even during acute ischemic events caused by thromboembolic events or trauma. A combination of the injury of hypoxia with the added insult of glutamate toxicity is therefore believed to be ultimately responsible for cellular death. Hence if the additive insult of glutamate toxicity can be alleviated, neurological damage could also be lessened. Anti-oxidants and anti-inflammatory agents have been proposed to reduce damage, but they often have poor access to structures such as the brain (which are protected by the blood brain barrier).

Given the importance of the NMDA, AMPA and kainate receptors in the mechanism of injury, research efforts have focused on using antagonists to these receptors to interfere with the receptor mediated calcium influx that ultimately leads to cellular death and tissue necrosis. In vitro studies using cultured neurons have demonstrated that glutamate receptor antagonists reduce neurotoxicity, but NMDA and AMPA/kainate receptor antagonists have different effects. Antagonists to NMDAr prevent neurotoxicity if present during the glutamate exposure period, but are less effective if added after glutamate is removed. In contrast, AMPA/kainate receptor antagonists are not as effective as NMDA antagonists during the glutamate exposure period, but are more effective following glutamate exposure.

Some of the research on these antagonists has focused on cannabinoids, a subset of which have been found to be NMDA receptor antagonists. U.S. Pat. No. 5,538,993 (3S, 4S-delta-6-tetrahydrocannabinol-7-oic acids), U.S. Pat. No. 5,521,215 (sterospecific (+) THC enantiomers), and U.S. Pat. No. 5,284,867 (dimethylheptyl benzopyrans) have reported that these cannabinoids are effective NMDA receptor blockers. U.S. Pat. No. 5,434,295 discloses that the 1,1 dimethylheptyl (DMH) homolog of [3R,4R]-7-hydroxy- $\Delta^6$THC (known as HU-210) is a superpotent cannabinoid receptor agonist with cannabinomimetic activity two orders of magnitude greater than the natural $\Delta^9$ THC. The HU-210 dimethylheptyl cannabinoid, has severe side effects, including fatigue, thirst, headache, and hypotension. *J. Pharmacol. Sci.* 60:1433–1457 (1971). Subjects who received this synthetic cannabinoid with a dimethylheptyl group experienced marked psychomotor retardation, and were unwilling or incapable of assuming an erect position.

In contrast to HU-210, the (−)(3R,4R) THC-DMH enantiomer (known as HU-211) displays low affinity to the cannabinoid receptors, but retains NMDA receptor antagonist neuroprotective activity.

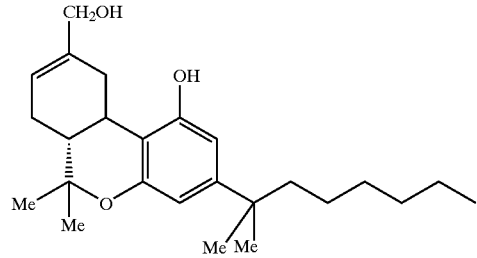

HU-211

THC (tetrahydrocannabinol) is another of the cannabinoids that has been shown to be neuroprotective in cell cultures, but this protection was believed to be mediated by interaction at the cannabinoid receptor, and so would be accompanied by undesired psychotropic side effects.

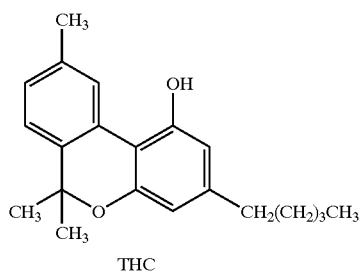

THC

Although it has been unclear whether cannabimimetic activity plays a role in neuroprotection against glutamate induced neurological injury, the teaching in this field has clearly been that a cannabinoid must at least be an antagonist at the NMDA receptor to have neuroprotective effect. Hence cannabidiol (2-[3-methyl-6-(1-methylethenyl)-2-cyclohexen-1-yl]-5-pentyl-1,3-benzenediol or CBD), a cannabinoid devoid of psychoactive effect (*Pharm. Rev.* 38:21–43, 1986), has not been considered useful as a neuroprotectant. Cannabidiol has been studied as an antiepileptic (Carlini et al., *J. Clin. Pharmacol.* 21:417S–427S, 1981; Karler et al., *J. Clin. Pharmacol.* 21:437S–448S, 1981, Consroe et al., *J. Clin Phannacol.* 21:428S–436S, 1981), and has been found to lower intraocular pressure (Colasanti et al, *Exp. Eye Res.* 39:251–259, 1984 and *Gen. Pharmac.* 15:479–484, 1984).

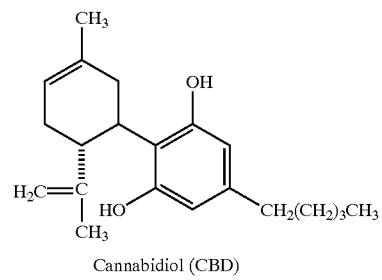

Cannabidiol (CBD)

No signs of toxicity or serious side effects have been observed following chronic administration of cannabidiol to healthy volunteers (Cunha et al., *Pharmacology* 21:175–185, 1980), even in large acute doses of 700 mg/day (Consroe et al., *Pharmacol. Biochem. Behav.* 40:701–708, 1991) but cannabidiol is inactive at the NMDA receptor. Hence in spite of its potential use in treating glaucoma and seizures, cannabidiol has not been considered a neuroprotective agent that could be used to prevent glutamate induced damage in the central nervous system.

SUMMARY OF THE INVENTION

It is an object of this invention to provide a new class of antioxidant drugs, that have particular application as neuroprotectants, although they are generally useful in the treatment of many oxidation associated diseases.

Yet another object of the invention is to provide a subset of such drugs that can be substantially free of psychoactive or psychotoxic effects, are substantially non-toxic even at very high doses, and have good tissue penetration, for example crossing the blood brain barrier.

It has surprisingly been found that cannabidiol and other cannabinoids can function as neuroprotectants, even though they lack NMDA receptor antagonist activity. This discovery was made possible because of the inventor's recognition of a previously unanticipated antioxidant property of the cannabinoids in general (and cannabidiol in particular) that functions completely independently of antagonism at the NMDA, AMPA and kainate receptors. Hence the present invention includes methods of preventing or treating diseases caused by oxidative stress, such as neuronal hypoxia, by administering a prophylactic or therapeutically effective amount of a cannabinoid to a subject who has a disease caused by oxidative stress.

The cannabinoid may be a cannabinoid other than THC, HU-210, or other potent cannabinoid receptor agonists. The cannabinoid may also be other than HU-211 or any other NMDA receptor antagonist that has previously been reported. A potent cannabinoid receptor agonist is one that has an $EC_{50}$ at the cannabinoid receptor of 50 nM or less, but in more particular embodiments 190 nM or 250 nM or less. In disclosed embodiments the cannabinoid is not psychoactive, and is not psychotoxic even at high doses. In some particularly disclosed embodiments, the cannabinoid is selected from the group:

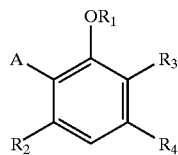

where A is aryl, and particularly

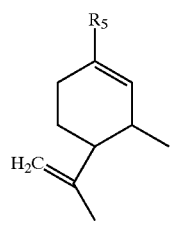

but not a pinene such as:

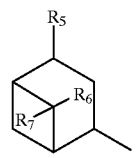

and the $R_1$–$R_5$ groups are each independently selected from the groups of hydrogen, lower substituted or unsubstituted alkyl, substituted or unsubstituted carboxyl, substituted or unsubstituted alkoxy, substituted or unsubstituted alcohol, and substituted or unsubstituted ethers, and $R_6$–$R_7$ are H or methyl. In particular embodiments, there are no nitrogens in the rings, and/or no amino substitutions on the rings.

In other embodiments, the cannabinoid is one of the following:

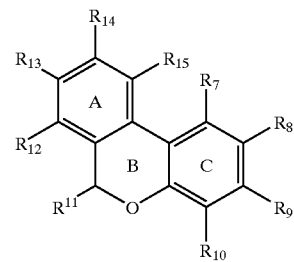

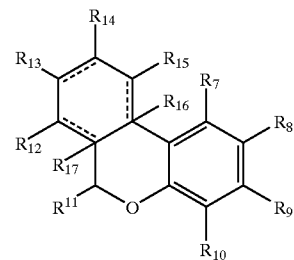

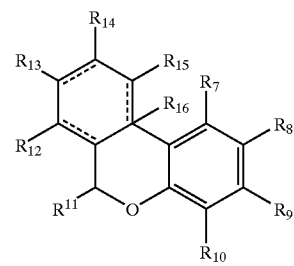

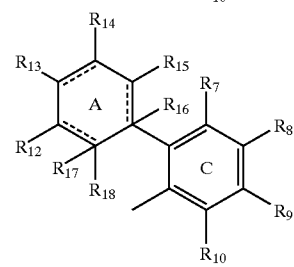

where there can be 0 to 3 double bonds on the A ring, as indicated by the optional double bonds indicated by dashed lines on the A ring. The C ring is aromatic, and the B ring can be a pyran. Particular embodiments are dibenzo pyrans and cyclohexenyl benzenediols. Particular embodiments of the cannabinoids of the present invention may also be highly lipid soluble, and in particular embodiments can be dissolved in an aqueous solution only sparingly (for example 10 mg/ml or less). The octanol/water partition ratio at neutral pH in useful embodiments is 5000 or greater, for example 6000 or greater. This high lipid solubility enhances penetration of the drug into the CNS, as reflected by its volume of distribution ($V_d$) of 1.5 L/kg or more, for example 3.5 L/kg, 7 L/kg, or ideally 10 L/kg or more, for example at least 20 L/kg. Particular embodiments may also be highly water soluble derivatives that are able to penetrate the CNS, for example carboxyl derivatives.

$R_{7-18}$ are independently selected from the group of H, substituted or unsubstituted alkyl, especially lower alkyl, for example unsubstituted $C_1$–$C_3$ alkyl, hydroxyl, alkoxy, especially lower alkoxy such as methoxy or ethoxy, substituted or unsubstituted alcohol, and unsubstituted or substituted carboxyl, for example COOH or $COCH_3$. In other embodiments $R_{7-18}$ can also be substituted or unsubstituted amino, and halogen.

The cannabinoid has substantially no binding to the NMDAr (for example an $IC_{50}$ greater than or equal to 5 $\mu M$ or 10 $\mu M$), has substantially no psychoactive activity mediated by the cannabinoid receptor (for example an $IC_{50}$ at the cannabinoid receptor of greater than or equal to 300 nM, for example greater than 1 $\mu M$ and a $K_i$ greater than 250 nM, especially 500–1000 nM, for example greater than 1000 nM), and antioxidant activity, as demonstratable by the Fenton reaction or cyclic voltametry.

In other particular embodiments, the cannabinoids are one of the following:

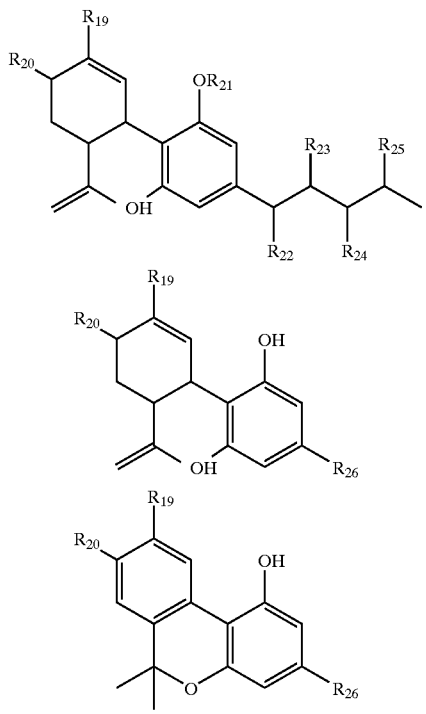

where $R_{19}$ is substituted or unsubstituted alkyl, such as lower alkyl (for example methyl), lower alcohol (such as methyl alcohol) or carboxyl (such as carboxylic acid) and oxygen (as in =O); $R_{20}$ is hydrogen or hydroxy; $R_{21}$ is hydrogen, hydroxy, or methoxy; $R_{22}$ is hydrogen or hydroxy; $R_{23}$ is hydrogen or hydroxy; $R_{24}$ is hydrogen or hydroxy; $R_{25}$ is hydrogen or hydroxy; and $R_{26}$ is substituted or unsubstituted alkyl (for example n-methyl alkyl), substituted or unsubstituted alcohol, or substituted or unsubstituted carboxy.

In yet other embodiments of the invention, the cannabinoids are

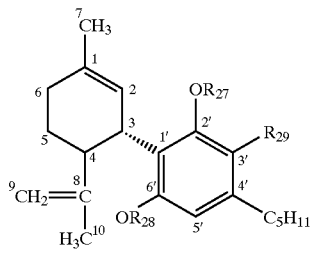

wherein numbering conventions for each of the ring positions are shown, and $R_{27}$, $R_{28}$ and $R_{29}$ are independently selected from the group consisting of H, unsubstituted lower alkyl such as $CH_3$, and carboxyl such as $COCH_3$. Particular examples of nonpsychoactive cannabinoids that fall within this definition are cannabidiol and

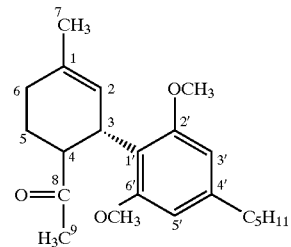

and other structural analogs of cannabidiol.

In more particular embodiments, the cannabinoid is used to prevent or treat an ischemic or neurodegenerative disease in the central nervous system of a subject, by administering to the subject a therapeutically effective amount of a cannabinoid to protect against oxidative injury to the central nervous system. The cannabinoid may be any of the compounds set forth above, or more specifically

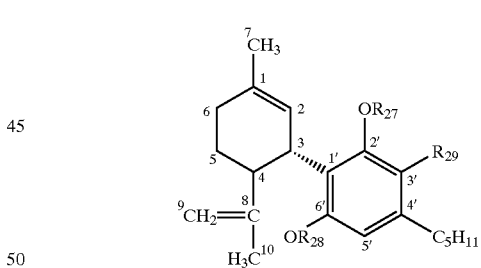

wherein $R_{27}$, $R_{28}$ and $R_{29}$ are independently selected from the group consisting of H, lower alkyl such as $CH_3$, and carboxyl such as $COCH_3$, and particularly wherein
a) $R_{27}=R_{28}=R_{29}=H$
b) $R_{27}=R_{29}=H$; $R_{28}=CH_3$
c) $R_{27}=R_{28}=CH_3$; $R_{29}=H$
d) $R_{27}=R_{28}=COCH_3$; $R_{29}=H$
e) $R_{27}=H$; $R_{28}=R_{29}=COCH_3$ When $R_{27}=R_{28}=R_{29}=H$, then the compound is cannabidiol. When $R_{27}=R_{29}=H$ and $R_{28}=CH_3$, the compound is CBD monomethyl ether. When $R_{27}=R_{28}=CH_3$ and $R_{29}=H$, the compound is CBD dimethyl ether. When $R_{27}=R_{28}=COCH_3$ and $R_{29}=H$, the compound is CBD diacetate. When $R_{27}=H$ and $R_{28}=R_{29}=COCH_3$, the compound is CBD monoacetate. The ischemic or neurodegenerative disease may be, for example, an ischemic infarct, Alzheimer's disease, Parkinson's disease, Down's syndrome, human immunodeficiency virus (HIV) dementia, myocardial infarction, or treatment and prevention of intraoperative or perioperative hypoxic insults that can leave persistent neurological deficits following open heart surgery requiring heart/lung bypass machines, such as coronary artery bypass grafts (CABG).

The invention also includes an assay for selecting a cannabinoid to use in treating a neurological disease by determining whether the cannabinoid is an antioxidant. Once it has been determined that the cannabinoid is an antioxidant, an antioxidant effective amount of the cannabinoid is administered to treat the neurological disease, such as a vascular ischemic event in the central nervous system, for example the type caused by a neurovascular thromboembolism. Similarly, the method of the present invention includes determining whether a disease is caused by oxidative stress, and if the disease is caused by oxidative stress, administering the cannabinoid in a therapeutically effective antioxidant amount.

The invention also includes identifying and administering antioxidant and neuroprotective compounds (such as cannabidiol) which selectively inhibit the enzyme activity of both 5- and 15-lipoxygenase more than the enzyme activity of 12-lipoxygenase. In addition, such compounds posses low NMDA antagonist activity and low cannabinoid receptor activity. Assays for selecting compounds with the desired effect on lipoxygenase enzymes, and methods for using identified compounds to treat neurological or ischemic diseases are also provided. Such diseases may include a vascular ischemic event in the central nervous system, for example a thromboembolism in the brain, or a vascular ischemic event in the myocardium. Useful administration of the compounds involves administration both during and after an ischemic injury.

These and other objects of the invention will be understood more clearly by reference to the following detailed description and drawings.

DETAILED DESCRIPTION OF SOME SPECIFIC EMBODIMENTS

Figure 1:
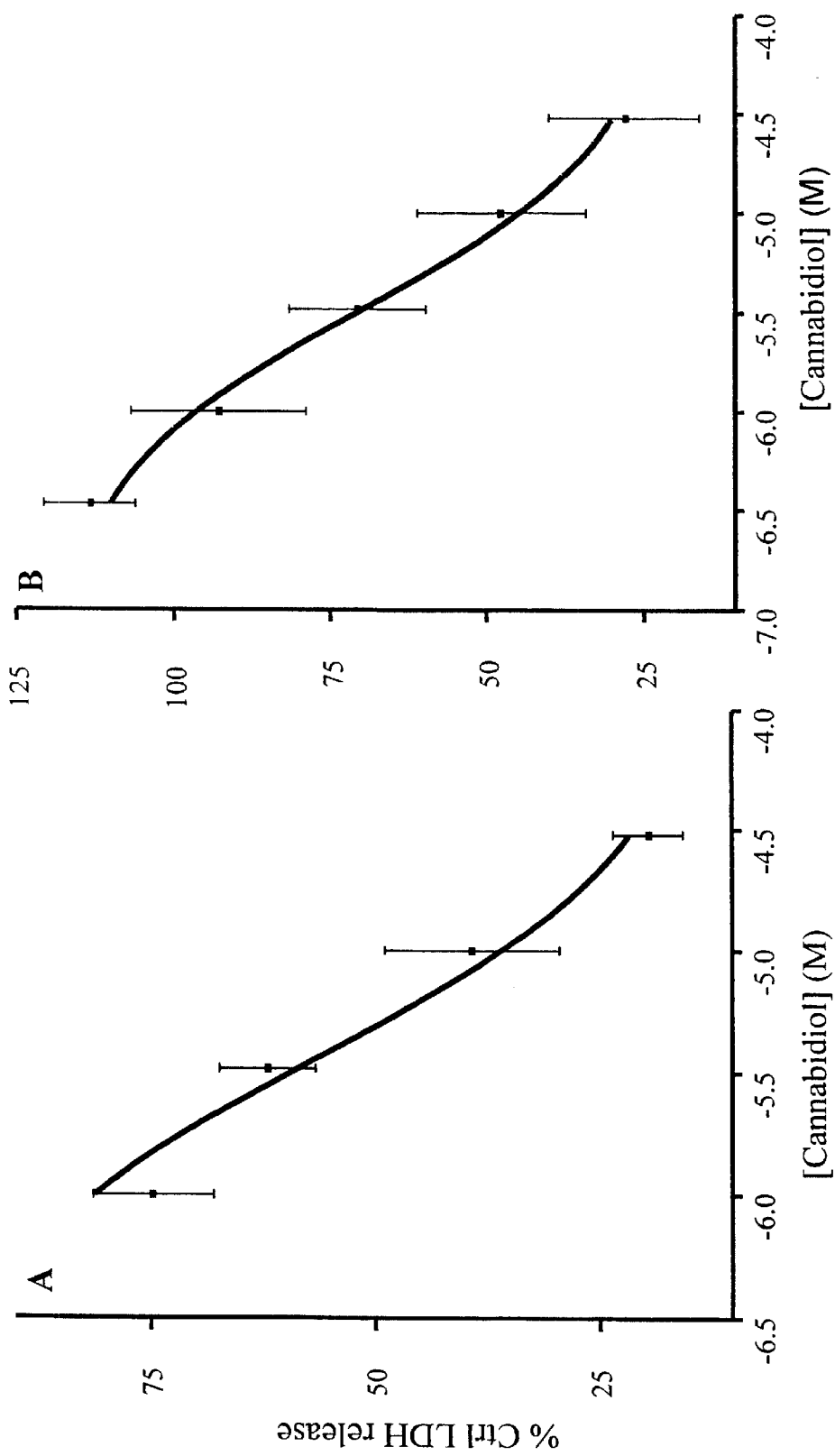
FIG. 1A is a graph showing NMDA induced cellular damage in a neuron (as measured by LDH release) in cells that were exposed to glutamate for 10 minutes, which demonstrates that increasing concentrations of cannabidiol in the cell culture protects against cellular damage.
FIG. 1B is a graph similar to FIG. 1A, but showing that AMPA/kainate receptor mediated damage (induced by glutamate and the AMPA/kainate receptor potentiating agents cyclothiazide or concanavalin A) is also reduced in a concentration dependent manner by the presence of cannabidiol in the culture medium.

This invention provides antioxidant compounds and compositions, such as pharmaceutical compositions, that include cannabinoids that act as free radical scavengers for use in prophylaxis and treatment of disease. The invention also includes methods for using the antioxidants in prevention and treatment of pathological conditions such as ischemia (tissue hypoxia), and in subjects who have been exposed to oxidant inducing agents such as cancer chemotherapy, toxins, radiation, or other sources of oxidative stress. The compositions and methods described herein are also used for preventing oxidative damage in transplanted organs, for inhibiting reoxygenation injury following reperfusion of ischemic tissues (for example in heart disease), and for any other condition that is mediated by oxidative or free radical mechanisms of injury. In particular embodiments of the invention, the compounds and compositions are used in the treatment of ischemic cardiovascular and neurovascular conditions, and neurodegenerative diseases. However the present invention can also be used as an antioxidant treatment in non-neurological diseases.

Molecular oxygen is essential for aerobic organisms, where it participates in many biochemical reactions, including its role as the terminal electron acceptor in oxidative phosphorylation. However excessive concentrations of various forms of reactive oxygen species and other free radicals can have serious adverse biological consequences, including the peroxidation of membrane lipids, hydroxylation of nucleic acid bases, and the oxidation of sulfhydryl groups and other protein moieties. Biological antioxidants include tocopherols and tocotrieneols, carotenoids, quinones, bilirubin, ascorbic acid, uric acid, and metal binding proteins. However these endogenous antioxidant systems are often overwhelmed by pathological processes that allow permanent oxidative damage to occur to tissue.

Free radicals are atoms, ions or molecules that contain an unpaired electron, are usually unstable, and exhibit short half-lives. Reactive oxygen species (ROS) is a collective term, designating the oxygen radicals (e.g. $.O_2^-$ superoxide radical), which by sequential univalent reduction produces hydrogen peroxide ($H_2O_2$) and hydroxyl radical (.OH). The hydroxyl radical sets off chain reactions and can interact with nucleic acids. Other ROS include nitric oxide (NO.) and peroxy nitrite (NOO.), and other peroxyl ($RO_2$.) and alkoxyl (RO.) radicals. Increased production of these poisonous metabolites in certain pathological conditions is believed to cause cellular damage through the action of the highly reactive molecules on proteins, lipids and DNA. In particular, ROS are believed to accumulate when tissues are subjected to ischemia, particularly when followed by reperfusion.

The pharmaceutical compositions of the present invention have potent antioxidant and/or free radical scavenging properties, that prevent or reduce oxidative damage in biological systems, such as occurs in ischemic/reperfusion injury, or in chronic neurodegenerative diseases such as Alzheimer's disease, HIV dementia, and many other oxidation associated diseases.

DEFINITIONS

"Oxidative associated diseases" refers to pathological conditions that result at least in part from the production of or exposure to free radicals, particularly oxyradicals, or reactive oxygen species. It is evident to those of skill in the art that most pathological conditions are multifactorial, and that assigning or identifying the predominant causal factors for any particular condition is frequently difficult. For these reasons, the term "free radical associated disease" encompasses pathological states that are recognized as conditions in which free radicals or ROS contribute to the pathology of the disease, or wherein administration of a free radical inhibitor (e.g. desferroxamine), scavenger (e.g. tocopherol, glutathione) or catalyst (e.g. superoxide dismutase, catalase) is shown to produce detectable benefit by decreasing symptoms, increasing survival, or providing other detectable clinical benefits in treating or preventing the pathological state.

Oxidative associated diseases include, without limitation, free radical associated diseases, such as ischemia, ischemic reperfusion injury, inflammatory diseases, systemic lupus erythematosis, myocardial ischemia or infarction, cerebrovascular accidents (such as a thromboembolic or hemorrhagic stroke) that can lead to ischemia or an infarct in the brain, operative ischemia, traumatic hemorrhage (for example a hypovolemic stroke that can lead to CNS hypoxia or anoxia), spinal cord trauma, Down's syndrome, Crohn's disease, autoimmune diseases (e.g. rheumatoid arthritis or diabetes), cataract formation, uveitis, emphysema, gastric ulcers, oxygen toxicity, neoplasia, undesired cellular apoptosis, radiation sickness, and others. The present invention is believed to be particularly beneficial in the treatment of oxidative associated diseases of the CNS, because of the ability of the cannabinoids to cross the blood brain barrier and exert their antioxidant effects in the brain. In particular embodiments, the pharmaceutical composition of the present invention is used for preventing, arresting, or treating neurological damage in Parkinson's disease, Alzheimer's disease and HIV dementia; autoimmune neurodegeneration of the type that can occur in encephalitis, and hypoxic or anoxic neuronal damage that can result from apnea, respiratory arrest or cardiac arrest, and anoxia caused by drowning, brain surgery or trauma (such as concussion or spinal cord shock).

As used herein, an "antioxidant" is a substance that, when present in a mixture containing an oxidizable substrate biological molecule, significantly delays or prevents oxidation of the substrate biological molecule. Antioxidants can act by scavenging biologically important reactive free radicals or other reactive oxygen species ($.O_2^-$, $H_2O_2$, .OH, HOCl, ferryl, peroxyl, peroxynitrite, and alkoxyl), or by preventing their formation, or by catalytically converting the free radical or other reactive oxygen species to a less reactive species. Relative antioxidant activity can be measured by cyclic voltametry studies of the type disclosed in Example 5 (and FIG. 3), where the voltage (x-axis) is an index of relative antioxidant activity. The voltage at which the first peak occurs is an indication of the voltage at which an electron is donated, which in turn is an index of antioxidant activity.

"Therapeutically effective antioxidant doses" can be determined by various methods, including generating an empirical dose-response curve, predicting potency and efficacy of a congener by using quantitative structure activity relationships (QSAR) methods or molecular modeling, and other methods used in the pharmaceutical sciences. Since oxidative damage is generally cumulative, there is no minimum threshold level (or dose) with respect to efficacy. However, minimum doses for producing a detectable therapeutic or prophylactic effect for particular disease states can be established.

As used herein, a "cannabinoid" is a chemical compound (such as cannabinol, THC or cannabidiol) that is found in the plant species *Cannabis saliva* (marijuana), and metabolites and synthetic analogues thereof that may or may not have psychoactive properties. Cannabinoids therefore include (without limitation) compounds (such as THC) that have high affinity for the cannabinoid receptor (for example $K_i$<250 nM), and compounds that do not have significant affinity for the cannabinoid receptor (such as cannabidiol, CBD). Cannabinoids also include compounds that have a characteristic dibenzopyran ring structure (of the type seen in THC) and cannabinoids which do not possess a pyran ring (such as cannabidiol). Hence a partial list of cannabinoids includes THC, CBD, dimethyl heptylpentyl cannabidiol (DMHP-CBD), 6,12-dihydro-6-hydroxy-cannabidiol (described in U.S. Pat. No. 5,227,537, incorporated by reference); (3S,4R)-7-hydroxy-$\Delta^6$-tetrahydrocannabinol homologs and derivatives described in U.S. Pat. No. 4,876,276, incorporated by reference; (+)-4-[4-DMH-2,6-diacetoxy-phenyl]-2-carboxy-6,6-dimethylbicyclo[3.1.1] hept-2-en, and other 4-phenylpinene derivatives disclosed in U.S. Pat. No. 5,434,295, which is incorporated by reference; and cannabidiol (−)(CBD) analogs such as (−)CBD-monomethylether, (−)CBD dimethyl ether; (−)CBD diacetate; (−)3'-acetyl-CBD monoacetate; and ±AF11, all of which are disclosed in Consroe et al., *J. Clin. Phannacol.*

21:428S–436S, 1981, which is also incorporated by reference. Many other cannabinoids are similarly disclosed in Agurell et al., *Pharmacol. Rev.* 38:31–43, 1986, which is also incorporated by reference.

As referred to herein, the term "psychoactivity" means "cannabinoid receptor mediated psychoactivity." Such effects include, euphoria, lightheadedness, reduced motor coordination, and memory impairment. Psychoactivity is not meant to include non-cannabinoid receptor mediated effects such as the anxiolytic effect of CBD.

The "lipoxygenase enzyme activity" refers to the relative level of lipoxygenase enzyme activity for a particular lipoxgenase, such as 5-, 15- or 12-lipoxygenase, as measured in Example 8. A compound would be said to "selectively inhibit a lipoxgenase enzyme" if the concentration of inhibitor required to reduce enzyme activity by 50% was at least about 5 times less than the amount required to reduce activity of a second lipoxgenase enzyme by the same degree (under the same conditions, i.e. temperature, substrate concentration, etc.)

An "antagonist" is a compound that binds and occupies a receptor without activating it. In the presence of a sufficient concentration of antagonist, an agonist cannot activate its receptor. Therefore, antagonists may decrease the neurotoxicity mediated by NMDA (as described in Example 3) or AMPA and Kainate (as described in Example 4).

An "agonist" is a compound that activates a receptor. When the receptor is activated for a longer than normal period of time, this may cause neurotoxicity, as in the case of NMDA, AMPA and kainate receptors (see Examples 3 and 4).

The term "alkyl" refers to a cyclic, branched, or straight chain alkyl group containing only carbon and hydrogen, and unless otherwise mentioned contains one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g. halogen, alkyl, alkoxy, alkylthio, trifluoromethyl, acyloxy, hydroxy, mercapto, carboxy, aryloxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to seven carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, hexyl and heptyl. Lower alkyl groups can also be unsubstituted or substituted, where a specific example of a substituted alkyl is 1,1-dimethyl heptyl.

"Hydroxyl" refers to —OH.

"Alcohol" refers to R—OH, wherein R is alkyl, especially lower alkyl (for example in methyl, ethyl or propyl alcohol). An alcohol may be either linear or branched, such as isopropyl alcohol.

"Carboxyl" refers to the radical —COOH, and substituted carboxyl refers to —COR where R is alkyl, lower alkyl or a carboxylic acid or ester.

The term "aryl" or "Ar" refers to a monovalent unsaturated aromatic carbocyclic group having a single ring (e.g. phenyl) or multiple condensed rings (e.g. naphthyl or anthryl), which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "alkoxy" refers to a substituted or unsubstituted alkoxy, where an alkoxy has the structure —O—R, where R is substituted or unsubstituted alkyl. In an unsubstituted alkoxy, the R is an unsubstituted alkyl. The term "substituted alkoxy" refers to a group having the structure —O—R, where R is alkyl which is substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of useful substituted alkoxy groups are: benzyloxy, naphthyloxy, and chlorobenzyloxy.

The term "aryloxy" refers to a group having the structure —O—Ar, where Ar is an aromatic group. A particular aryloxy group is phenoxy.

The term "heterocycle" refers to a monovalent saturated, unsaturated, or aromatic carbocyclic group having a single ring (e.g. morpholino, pyridyl or faryl) or multiple condensed rings (e.g. indolizinyl or benzo[b]thienyl) and having at least one heteroatom, defined as N, O, P, or S, within the ring, which can optionally be unsubstituted or substituted with, e.g. halogen, alkyl, alkoxy, alkylthio, trifluoromethyl, acyloxy, hydroxy, mercapto, carboxy, aryloxy, aryl, arylakyl, heteroaryl, amino, alkylamino, dialkylamino, morpholino, piperidino, pyrrolidin-1-yl, piperazin-1-yl, or other functionality.

"Arylalkyl" refers to the groups —R—Ar and —R—HetAr, where Ar is an aryl group. HetAr is a heteroaryl group, and R is a straight-chain or branched chain aliphatic group. Example of arylaklyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, peperidino, pyrrolidin-1-yl, piperazin-1-yl, or other functionality.

The term "halo" or "halide" refers to fluoro, bromo, chloro and iodo substituents.

The term "amino" refers to a chemical functionality —NR'R" where R' and R" are independently hydrogen, alkyl, or aryl. The term "quaternary amine" refers to the positively charged group —N$^+$R'R", where R'R" and R" are independently selected and are alkyl or aryl. A particular amino group is —NH$_2$.

A "pharmaceutical agent" or "drug" refers to a chemical compound or composition capable of inducing a desired therapeutic or prophylactic effect when properly administered to a subject.

All chemical compounds include both the (+) and (−) stereoisomers, as well as either the (+) or (−) stereoisomer.

Other chemistry terms herein are used according to conventional usage in the art, as exemplified by *The McGraw-Hill Dictionary of Chemical Terms* (1985) and *The Condensed Chemical Dictionary* (1981).

The following examples show that both nonpsychoactive cannabidiol, and psychoactive cannabinoids such as THC, can protect neurons from glutamate induced death, by a mechanism independent of cannabinoid receptors. Cannabinoids are also be shown to be potent antioxidants capable of preventing ROS toxicity in neurons.

EXAMPLE 1

Preparation of Cannabinoids and Neuronal Cultures

Cannabidiol, THC and reactants other than those specifically listed below were purchased from Sigma Chemical, Co. (St. Louis, Mo.). Cyclothiazide, glutamatergic ligands and MK-801 were obtained from Tocris Cookson (UK). Dihydrorhodamine was supplied by Molecular Probes (Eugene, Oreg.). T-butyl hydroperoxide, tetraethylammonium chloride, ferric citrate and sodium dithionite were all purchased from Aldrich (WI). All culture media were Gibco/BRL (MD) products.

Solutions of cannabinoids, cyclothiazide and other lipophiles were prepared by evaporating a 10 mM ethanolic solution (under a stream of nitrogen) in a siliconized microcentrifuge tube. Dimethyl sulfoxide (DMSO, less than 0.05% of final volume) was added to ethanol to prevent the lipophile completely drying onto the tube wall. After evaporation, 1 ml of culture media was added and the drug was dispersed using a high power sonic probe. Special attention was used to ensure the solution did not overheat or generate foam. Following dispersal, all solutions were made up to their final volume in siliconized glass tubes by mixing with an appropriate quantity of culture media.

Primary neuronal cultures were prepared according to the method of Ventra et al. (J. Neurochem. 66:1752–1761, 1996). Fetuses were extracted by Cesarian section from a 17 day pregnant Wistar rat, and the feral brains were placed into phosphate buffered saline. The cortices were then dissected out, cut into small pieces and incubated with papain for nine minutes at 37° C. After this time the tissue was dissociated by passage through a fire polished Pasteur pipette, and the resultant cell suspension separated by centrifugation over a gradient consisting of 10 mg/ml bovine serum albumin and 10 mg/ml ovomucoid (a trypsin inhibitor) in Earls buffered salt solution. The pellet was then re-suspended in high glucose, phenol red free Dulbeco's modified Eagles medium containing 10% fetal bovine serum, 2 mM glutamine, 100 IU penicillin, and 100 µg/ml streptomycin (DMEM). Cells were counted, tested for vitality using the trypan blue exclusion test and seeded onto poly-D-lysine coated 24 multiwell plates. After 96 hours, 10 µM fluoro-deoxyuridine and 10 µM uridine were added to block glial cell growth. This protocol resulted in a highly neuron-enriched culture.

EXAMPLE 2

Preparation of Astrocytes and Conditioned Media

Astrocyte conditioned DMEM was used throughout the AMPA/kainate toxicity procedure and following glutamate exposure in the NMDAr mediated toxicity protocol. Media was conditioned by 24 hour treatment over a confluent layer of type I astrocytes, prepared from two day old Wistar rat pups. Cortices were dissected, cut into small pieces, and enzymatically digested with 0.25% trypsin. Tissue was then dissociated by passage through a fire polished Pasteur pipette and the cell suspension plated into untreated 75 cm² T-flasks. After 24 hours the media was replaced and unattached cells removed. Once astrocytes achieved confluence, cells were divided into four flasks. Media for experiments was conditioned by a 24 hour exposure to these astrocytes, after which time it was frozen at −20° C. until use. Astrocyte cultures were used to condition DMEM for no longer than two months.

EXAMPLE 3

NMDA Mediated Toxicity Studies

Glutamate neurotoxicity can be mediated by NMDA, AMPA or kainate receptors. To examine NMDAr mediated toxicity, cultured neurons (cultured for 14–18 days) were exposed to 250 µM glutamate for 10 minutes in a magnesium free saline solution. The saline was composed of 125 mM NaCl, 25 mM glucose, 10 mM HEPES (pH 7.4), 5 mM KCl, 1.8 mM calcium chloride and 5% bovine serum albumin. Following exposure, cells were washed twice with saline, and incubated for 18 hours in conditioned DMEM. The level of lactate dehydrogenase (LDH) in the media was used as an index of cell injury.

Toxicity was completely prevented by addition of the NMDAr antagonist, MK-801 (500 nM, data not shown). However, FIG. 1A shows that cannabidiol also prevented neurotoxicity (maximum protection 88±9%) with an $EC_{50}$ of 2–4 µM (specifically about 3.5 µM).

EXAMPLE 4

AMPA and Kainate Receptor Mediated Toxicity Studies

Unlike NMDA receptors, which are regulated by magnesium ions, AMPA/kainate receptors rapidly desensitize following ligand binding. To examine AMPA and kainate receptor mediated toxicity, neurons were cultured for 7–13 days, then exposed to 100 µM glutamate and 50 µM cyclothiazide (used to prevent AMPA receptor desensitization). Cells were incubated with glutamate in the presence of 500 nM MK-801 (an NMDAr antagonist) for 18–20 hours prior to analysis. Specific AMPA and kainate receptor ligands were also used to separately examine the effects of cannabinoids on AMPA and kainate receptor mediated events. Fluorowillardiine (1.5 µM) was the AMPA agonist and 4-methyl glutamate (10 µM) was the kainate agonist used to investigate receptor mediated toxicity. When specifically examining kainate receptor activity, cyclothiazide was replaced with 0.15 mg/ml Concanavalin-A.

Cannabidiol protection against AMPA/kainate mediated neurotoxicity is illustrated in FIG. 1B, where LDH in the media was used as an index of cell injury. The neuroprotective effect of cannabidiol was similar to that observed in the NMDA mediated toxicity model (FIG. 1A). Cannabidiol prevented neurotoxicity (maximum protection 80±17%) with an $EC_{50}$ of 2–4 µM (specifically about 3.3 µM). Comparable results were obtained with either the AMPA receptor ligand, fluorowillardiine or the kainate receptor specific ligand, 4-methyl-glutamate (data not shown). Hence cannabidiol protects similarly against toxicity mediated by NMDA, AMPA or kainate receptors.

Figure 2:
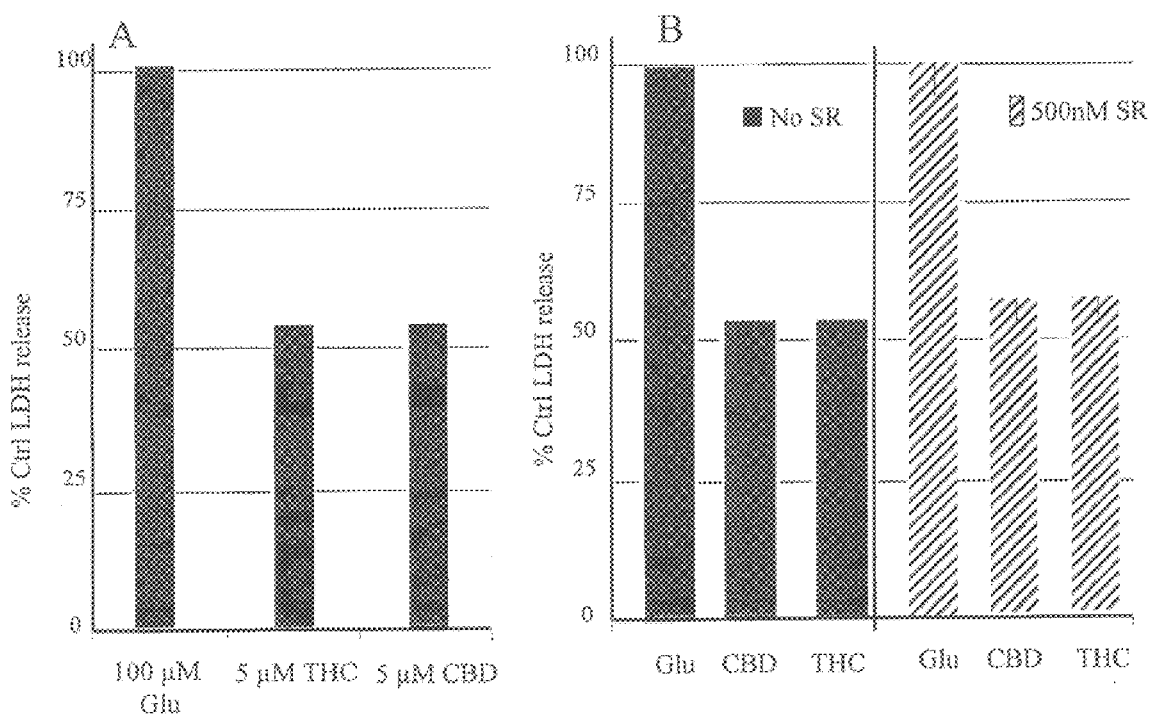
FIG. 2A is a bar graph showing cellular damage (as measured by LDH release) in the presence of glutamate alone (100 $\mu$M Glu), and in the presence of glutamate and 5 $\mu$M cannabidiol (CBD) or 5 $\mu$M THC, and demonstrates that CBD and THC were similarly protective.
FIG. 2B is a bar graph similar to FIG. 2A, but showing the cellular damage assessed in the presence of the cannabinoid receptor antagonist SR 141716A (SR), which was not found to alter the neuroprotective effect of CBD (5 $\mu$M) or THC (5 $\mu$M), indicating the effect is not a typical cannabinoid effect mediated by the cannabinoid receptor.

Unlike cannabidiol, THC is a ligand (and agonist) for the brain cannabinoid receptor. The action of THC at the cannabinoid receptor has been proposed to explain the ability of THC to protect neurons from NMDAr toxicity in vitro. However in AMPA/kainate receptor toxicity assays, THC and cannabidiol were similarly protective (FIG. 2A), indicating that cannabinoid neuroprotection is independent of cannabinoid receptor activation. This was confirmed by inclusion of cannabinoid receptor antagonist SR-141716A in the culture media (SR in FIG. 2B). See Mansbach et al., Psychopharmacology 124:315–22, 1996, for a description of SR-141716A. Neither THC nor cannabidiol neuroprotection was affected by cannabinoid receptor antagonist (FIG. 2B).

EXAMPLE 5

Cyclic Voltametery Studies or ReDox Potentials

To investigate whether cannabinoids protect neurons against glutamate damage by reacting with ROS, the antioxidant properties of cannabidiol and other cannabinoids were assessed. Cyclic voltametry, a procedure that measures the ability of a compound to accept or donate electrons under a variable voltage potential, was used to measure the oxidation potentials of several natural and synthetic cannabinoids. These studies were performed with an EG&G Princeton Applied Research potentiostat/galvanostat (Model 273/PAR 270 software, NJ). The working electrode was a glassy carbon disk with a platinum counter electrode and silver/silver chloride reference. Tetraethylammonium chloride in acetonitrile (0.1 M) was used as an electrolyte. Cyclic voltametry scans were done from +0 to 1.8 V at scan rate of 100 mV per second. The reducing ability of cannabidiol (CBD), THC, HU-211, and BHT were measured in this fashion. Anandamide, a cannabinoid receptor ligand without a cannabinoid like structure, was used as a non-responsive control. Each experiment was repeated twice with essentially the same results.

Figure 3:
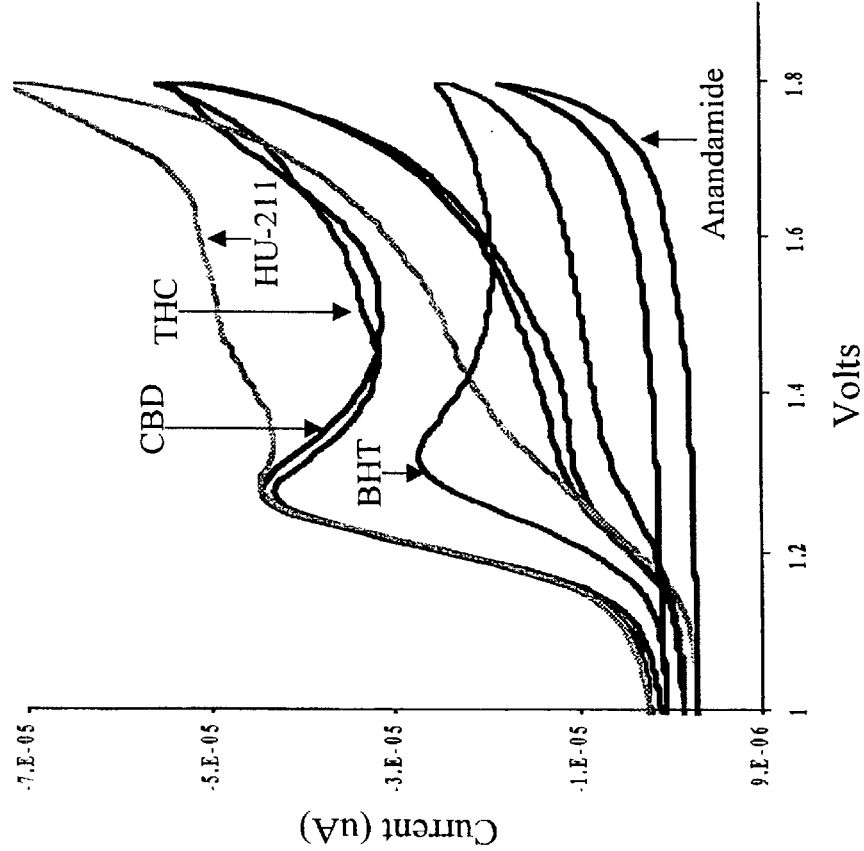
FIG. 3 is a graph showing the reduction oxidation potentials determined by cyclic voltametry for some natural and synthetic cannabinoids, the antioxidant BHT, and the non-cannabinoid anandamide (arachidonyl ethanolamide) which is a ligand for the cannabinoid receptor. The voltage at which initial peaks occur is an indication of antioxidant activity.

Cannabidiol, THC and the synthetic cannabinoid HU-211 all donated electrons at a similar potential as the antioxidant BHT. Anandamide (arachidonyl ethanolamide) did not undergo oxidation at these potentials (FIG. 3). Several other natural and synthetic cannabinoids, including cannabidiol, nabilone, and levanantrodol were also tested, and they too exhibited oxidation profiles similar to cannabidiol and THC (data not shown).

EXAMPLE 6

Iron Catalyzed Dihydrorhodamine Oxidation (Fenton Reaction)

The ability of cannabinoids to be readily oxidized, as illustrated in Example 5, indicated they possess antioxidant properties comparable to BHT. The antioxidant activity of BHT was examined in a Fenton reaction, in which iron is catalyzed to produce ROS. Cannabidiol (CBD) and tetrahydrocannabinol (THC) were evaluated for their ability to prevent oxidation of dihydrorhodamine to the fluorescent compound rhodamine. Oxidant was generated by ferrous catalysis (diothionite reduced ferric citrate) of t-butyl hydroperoxide in a 50:50 water:acetonitrile (v/v) solution. Dihydrorhodamine (50 $\mu$M) was incubated with 300 $\mu$M t-butyl hydroperoxide and 0.5 $\mu$M iron for 5 minutes. After this time, oxidation was assessed by spectrofluorimetry (Excit=500 nm, Emiss=570 nm). Various concentrations of cannabinoids and BHT were included to examine their ability to prevent dihydrorhodiamine oxidation.

Figure 4:
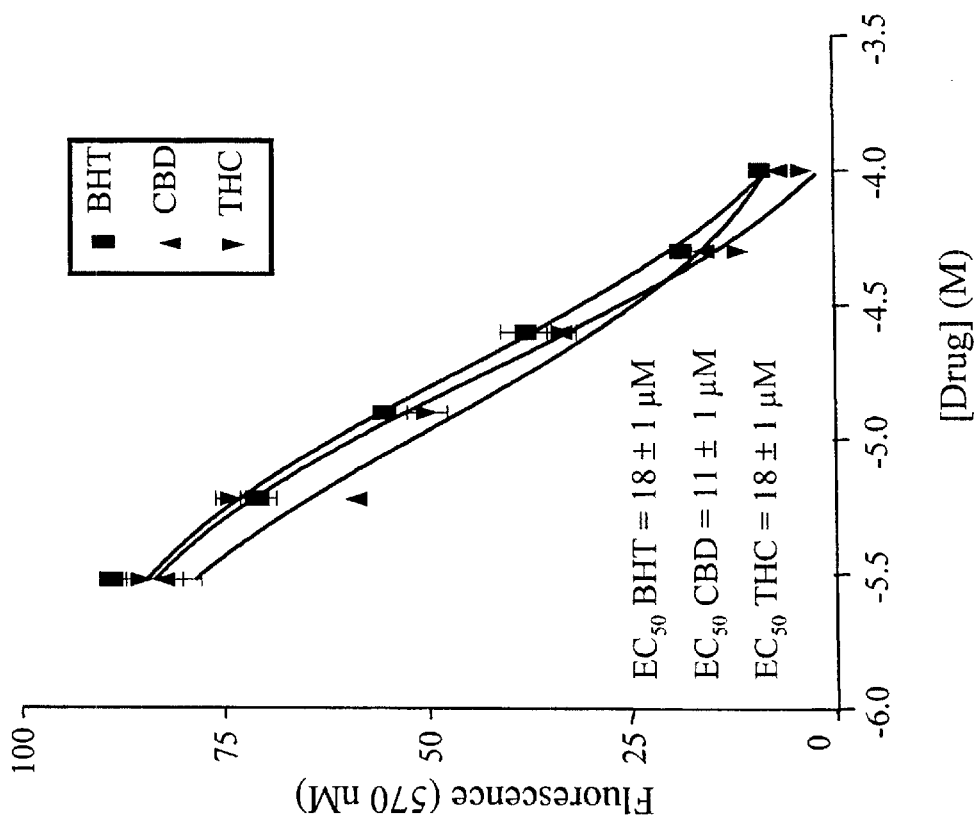
FIG. 4 is a graph that demonstrates the antioxidant properties of BHT, CBD and THC, by plotting the fluorescence of a fluorescent dye against concentrations of these substances, where declining fluorescence is an indication of greater antioxidant activity.

Cannabidiol, THC and BHT all prevented dihydrorhodamine oxidation in a similar, concentration dependent manner (FIG. 4), indicating that cannabinoids have antioxidant potency comparable to BHT.

Figure 5:
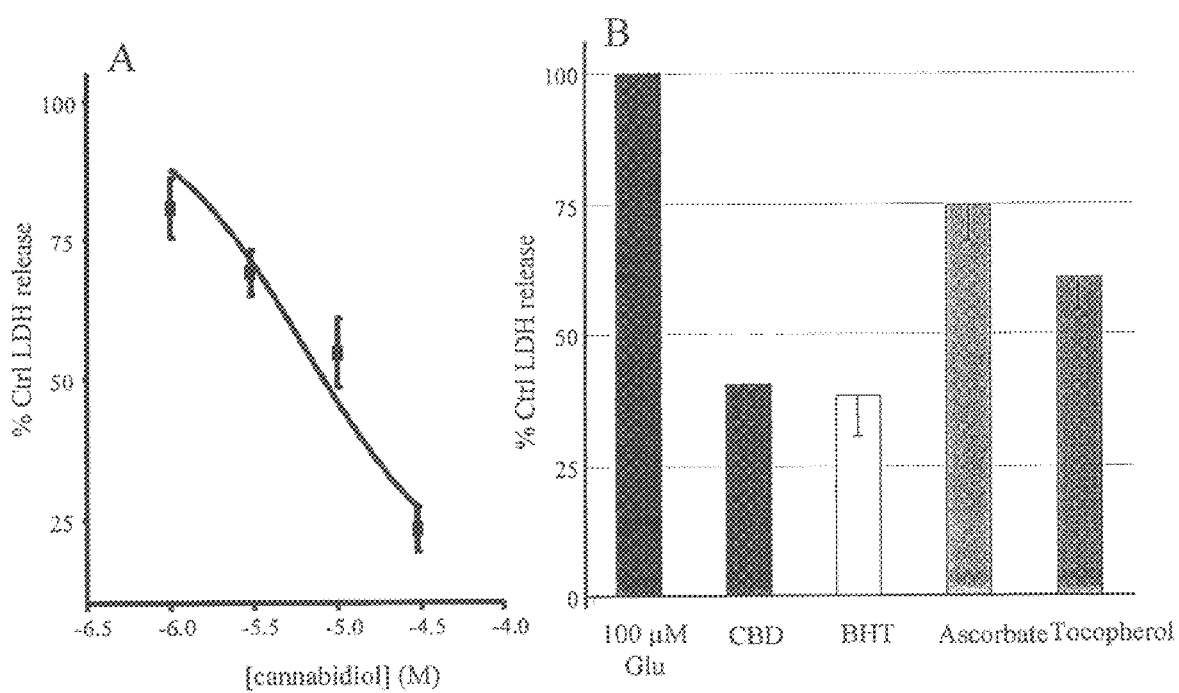
FIG. 5A is a graph illustrating decreased t-butyl peroxide induced toxicity (as measured by LDH release) in the presence of increasing concentrations of cannabidiol, demonstrating that cannabidiol is an effective antioxidant in living cells.
FIG. 5B is a bar graph comparing the antioxidant activity of several antioxidants against glutamate induced toxicity in neurons, showing that CBD has superior antioxidant activity.

To confirm that cannabinoids act as antioxidants in the intact cell, neurons were also incubated with the oxidant t-butyl hydroperoxide and varying concentrations of cannabidiol (FIG. 5A). The t-butyl hydroperoxide oxidant was chosen for its solubility in both aqueous and organic solvents, which facilitates oxidation in both cytosolic and membrane cell compartments. Cell toxicity was assessed 18–20 hours after insult by measuring lactate dehydrogenase (LDH) release into the culture media. All experiments were conducted with triple or quadruple values at each point and all plates contained positive (glutamate alone) and baseline controls. The assay was validated by comparison with an XTT based metabolic activity assay. As shown in FIG. 5A, cannabidiol protected neurons against ROS toxicity in a dose related manner, with an $EC_{50}$ of about 6 $\mu$M. The maximum protection observed was 88±9%.

Cannabidiol was also compared with known antioxidants in an AMPA/kainate toxicity protocol. Neurons were exposed to 100 $\mu$M glutamate and equimolar (5 $\mu$M) cannabidiol, α-tocopherol, BHT or ascorbate (FIG. 5B). Although all of the antioxidants attenuated glutamate toxicity, cannabidiol was significantly more protective than either α-tocopherol or ascorbate. The similar antioxidant abilities of cannabidiol and BHT in this chemical system (FIG. 4), and their comparable protection in neuronal cultures (FIG. 5B), implies that cannabidiol neuroprotection is due to an antioxidant effect.

EXAMPLE 7

In vivo Rat Studies

The middle cerebral artery of chloral hydrate anesthetized rats was occluded by insertion of suture thread into it. The animals were allowed to recover from the anesthetic and move freely for a period of two hours. After this time the suture was removed under mild anesthetic and the animals allowed to recover for 48 hours. Then the animals were tested for neurological deficits, sacrificed, and the infarct volume calculated. To examine the infarct volume, animals were anesthetized, ex-sanguinated, and a metabolically active dye (3-phenyl tetrazolium chloride) was pumped throughout the body. All living tissues were stained pink by the dye, while morbid regions of infarcted tissue remained white. Brains were then fixed for 24 hours in formaldehyde, sliced and the infarct volumes measured.

One hour prior to induction of ischemia 20 mg/kg of cannabidiol was administered by intra-peritoneal injection (ip) in a 90% saline:5% emulphor 620 (emulsifier):5% ethanol vehicle. A second ip 10 mg/kg dose of cannabidiol was administered 8 hours later using the same vehicle. Control animals received injections of vehicle without drug. IV doses would be expected to be 3–5 times less because of reduction of first pass metabolism.

The infarct size and neurological assessment of the test animals is shown Table 1.

TABLE 1

Cannabidiol protects rat brains from ischemia damage

| | Volume of Infarct (mm3) | | Behavioral Deficit Score | |
|---|---|---|---|---|
| Animal | Drug | Control | Drug | Control |
| 1 | 108.2 | 110.5 | 3 | 2 |
| 2 | 83.85 | 119.6 | 4 | 4 |
| 3 | 8.41 | 118.9 | 3 | 4 |
| 4 | 75.5 | 177.7 | 1 | 4 |
| 5 | 60.53 | 33.89 | 1 | 3 |
| 6 | 27.52 | 255.5 | 1 | 5 |
| 7 | 23.16 | 143 | 1 | 4 |
| Mean | 55.3 | 137.0 | 2.0 | 3.7 |
| SEM | 13.8 | 25.7 | 0.5 | 0.4 |
| | p = 0.016 significant | | p = 0.015 significant | |

*Neurological scoring is performed on a subjective 1–5 scale of impairment. 0 = no impairment, 5 = severe (paralysis)

This data shows that infarct size was approximately halved in the animals treated with cannabidiol, which was also accompanied by a substantial improvement in the neurological status of the animal.

These studies with the nonpsychotropic marijuana constituent, cannabidiol, demonstrate that protection can be achieved against both glutamate neurotoxicity and free radical induced cell death. THC, the psychoactive principle of cannabis, also blocked glutamate neurotoxicity with a potency similar to cannabidiol. In both cases, neuroprotection is unaffected by the presence of a cannabinoid receptor antagonist. These results therefore surprisingly demonstrate that cannabinoids can have useful therapeutic effects that are not mediated by cannabinoid receptors, and therefore are not necessarily accompanied by psychoactive side effects. Cannabidiol also acts as an anti-epileptic and anxiolytic, which makes it particularly useful in the treatment of neurological diseases in which neuroanatomic defects can predispose to seizures (e.g. subarachnoid hemorrhage).

A particular advantage of the cannabinoid compounds of the present invention is that they are highly lipophilic, and have good penetration into the central nervous system. The volume of distribution of some of these compounds is at least 100 L in a 70 kg person (1.4 L/kg), more particularly at least 250 L, and most particularly 500 L or even 700 L in a 70 kg person (10 L/kg). The lipophilicity of particular compounds is also about as great as that of THC, cannabidiol or other compounds that have excellent penetration into the brain and other portions of the CNS.

Cannabinoids that lack psychoactivity or psychotoxicity are particularly useful embodiments of the present invention, because the absence of such side effects allows very high doses of the drug to be used without encountering unpleasant side effects (such as dysphoria) or dangerous complications (such as obtundation in a patient who may already have an altered mental status). For example, therapeutic antioxidant blood levels of cannabidiol can be 5–20 mg/kg, without significant toxicity, while blood levels of psychoactive cannabinoids at this level would produce obtundation, headache, conjunctival irritation, and other problems. Particular examples of the compounds of the present invention have low affinity to the cannabinoid receptor, for example a $K_i$ of greater than 250 nM, for example $K_i \geq 500-1000$ nM. A compound with a $K_i \geq 1000$ nM is particularly useful, which compound has essentially no psychoactivity mediated by the cannabinoid receptor.

Cannabidiol blocks glutamate toxicity with equal potency regardless of whether the insult is mediated by NMDA, AMPA or kainate receptors. Cannabidiol and THC have been shown to be comparable to the antioxidant BHT, both in their ability to prevent dihydrorhodamine oxidation and in their cyclic voltametric profiles. Several synthetic cannabinoids also exhibited profiles similar to the BHT, although anandamide, which is not structurally related to cannabinoids, did not. These findings indicate that cannabinoids act as antioxidants in a non-biological situation, which was confirmed in living cells by showing that cannabidiol attenuates hydroperoxide induced neurotoxicity. The potency of cannabidiol as an antioxidant was examined by comparing it on an equimolar basis with three other commonly used compounds.

In the AMPA/kainate receptor dependent neurotoxicity model, cannabidiol neuroprotection was comparable to the potent antioxidant, BHT, but significantly greater than that observed with either α-tocopherol or ascorbate. This unexpected superior antioxidant activity (in the absence of BHT tumor promoting activity) shows for the first time that cannabidiol, and other cannabinoids, can be used as antioxidant drugs in the treatment (including prophylaxis) of oxidation associated diseases, and is particularly useful as a neuroprotectant. The therapeutic potential of nonpsychoactive cannabinoids is particularly promising, because of the absence of psychotoxicity, and the ability to administer higher doses than with psychotropic cannabinoids, such as THC. Previous studies have also indicated that cannabidiol is not toxic, even when chronically administered to humans or given in large acute doses (700 mg/day).

EXAMPLE 8

Effect of Cannabidiol on Lipoxygenase Enzymes

This example describes in vitro and in vivo assays to examine the effect of cannabidiol (CBD) on three lipoxygenase (LO) enzymes: 5-LO, 12-LO and 15-LO.

In vitro Enzyme Assay

The ability of CBD to inhibit lipoxygenase was examined by measuring the time dependent change in absorption at 234 nM following addition of 5 U of each lipoxygenase (rabbit 15-LO purchased from Biomol (PA), porcine 12-LO purchased from Cayman chemicals (MI)) to a solution containing 10 µM (final concentration) linoleic acid.

Enzyme studies were performed using a u.v. spectrophotometer and a 3 ml quartz cuvette containing 2.5 ml of a stirred solution of 12.5 µM sodium linoleic acid (sodium salt) in solution A (25 mM Tris (pH 8.1), 1 mM EDTA 0.1% methyl cellulose). The reaction was initiated by addition of 0.5 ml enzyme solution (10 U/ml enzyme in solution A) and recorded for 60 seconds. Lipoxygenase exhibits non-Michaelis-Menten kinetics, an initial "lag" (priming) phase followed by a linear phase which is terminated by product inhibition. These complications were reduced by assessing enzyme activity (change in absorption) over the "steepest" 20 second period in a 60 second run time. Recordings examined the absorption at 234 nm minus the value at a reference wavelength of 280 nm. Linoleic acid was used as the substrate rather than arachidonic acid, because the products are less inhibitory to the enzyme, thereby providing a longer "linear phase".

Cell Purification and Separation

Human platelets and leukocytes were purified from buffy coat preparations (NIH Blood Bank) using a standard Ficoll based centrifugation method used in blood banks. Prior to use, cells were washed three times to eliminate contaminating cell types. Cultured rat basophillic leukemia cells (RBL-2H3) were used as a source of 5-lipoxygenase.

In vivo Determination of Lipoxygenase Activity

Cells were incubated with arachidonic acid and stimulated with the calcium ionophore A23187. Lipids were extracted and separated by reverse phase HPLC. Product formation was assessed as the area of a peak that co-eluted with an authentic standard, had a greater absorbance at 236 nm than at either 210 or 280 nm, and the formation of which was inhibited by a lipoxygenase inhibitor.

Cell pellets were triturated in DMEM culture media, aliquoted and pre-incubated for 15 minutes with 20 µM arachidonic acid and varying concentrations of cannabidiol and/or 40 µM nordihydroguaiaretic acid (a lipxygenase inhibitor). Platelets and leukocytes were also pre-incubated with 80 µM manoalide (Biomol) to prevent phospholipase A2 activation. Product formation was initiated by addition of 5 µM A23187 and incubation for 10 minutes at 37° C. At the end of the incubation, the reaction was stopped by addition of 15% 1M HCl and 10 ng/ml prostaglandin B2 (internal standard). Lipids were extracted with 1 volume of ethyl ether, which was dried under a stream of nitrogen. Samples were reconstituted in 50% acetonitrile:50% $H_2O$ and separated by reverse phase HPLC using a gradient running from 63% acetonitrile: 37% $H_2O$:0.2% acetic acid to 90% acetonitrile (0.2% acetic acid) over 13 minutes.

Measurement of NMDAr Toxicity

The ability of 12-HETE (12-(s)-hydroxy-eicosatetraenoic acid, the product of the action of 12-lipoxygenase on arachidonic (eicosatetraenoic) acid) to protect cortical neurons from NMDAr toxicity was measured as described in Example 3. The 12-HETE (0.5 µg/ml) was added either during ischemia (co-incubated with the glutamate), during post-ischemia (co-incubated with the DMEM after washing the cells), or during both ischemia and post-ischemia.

Results

Figure 6:
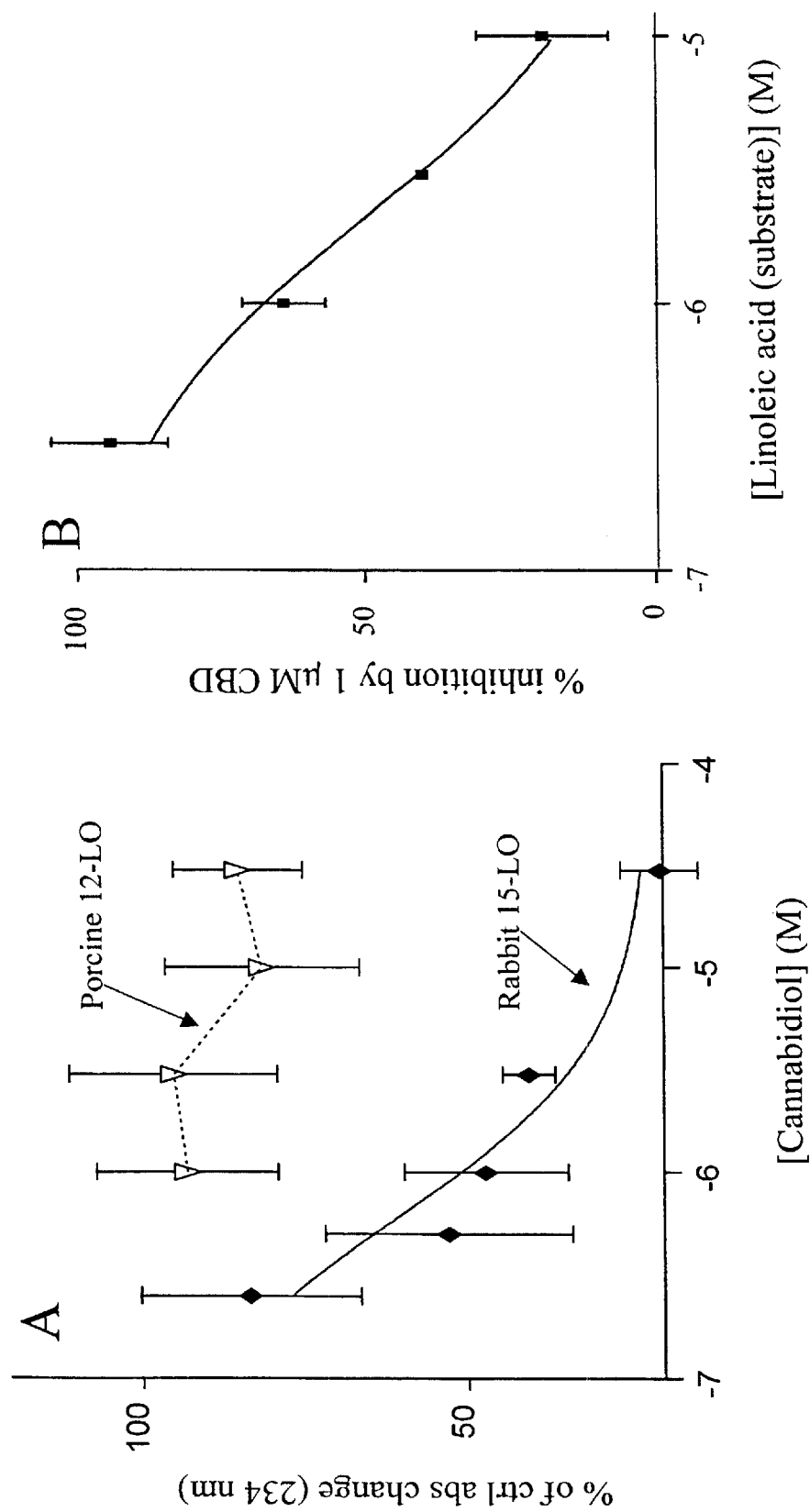
FIG. 6A is a graph showing the effect of CBD (as measured by the change in absorbance at 234 nm) on the enzymatic activity of two lipoxygenase enzymes, rabbit 15-LO and porcine 12-LO, which demonstrates that CBD inhibits 15-LO, but not 12-LO enzyme.
FIG. 6B is a graph demonstrating that inhibitory effect of CBD on 15-LO is competitive.

Using semi-purified enzyme preparations, the effect of CBD on rabbit 15-LO and porcine 12-LO was compared. As shown in FIGS. 6A and B, CBD is a potent competitive inhibitor of 15-LO with an $EC_{50}$ of 598 nM. However, CBD had no effect on the 12-LO enzyme.

Figure 7:
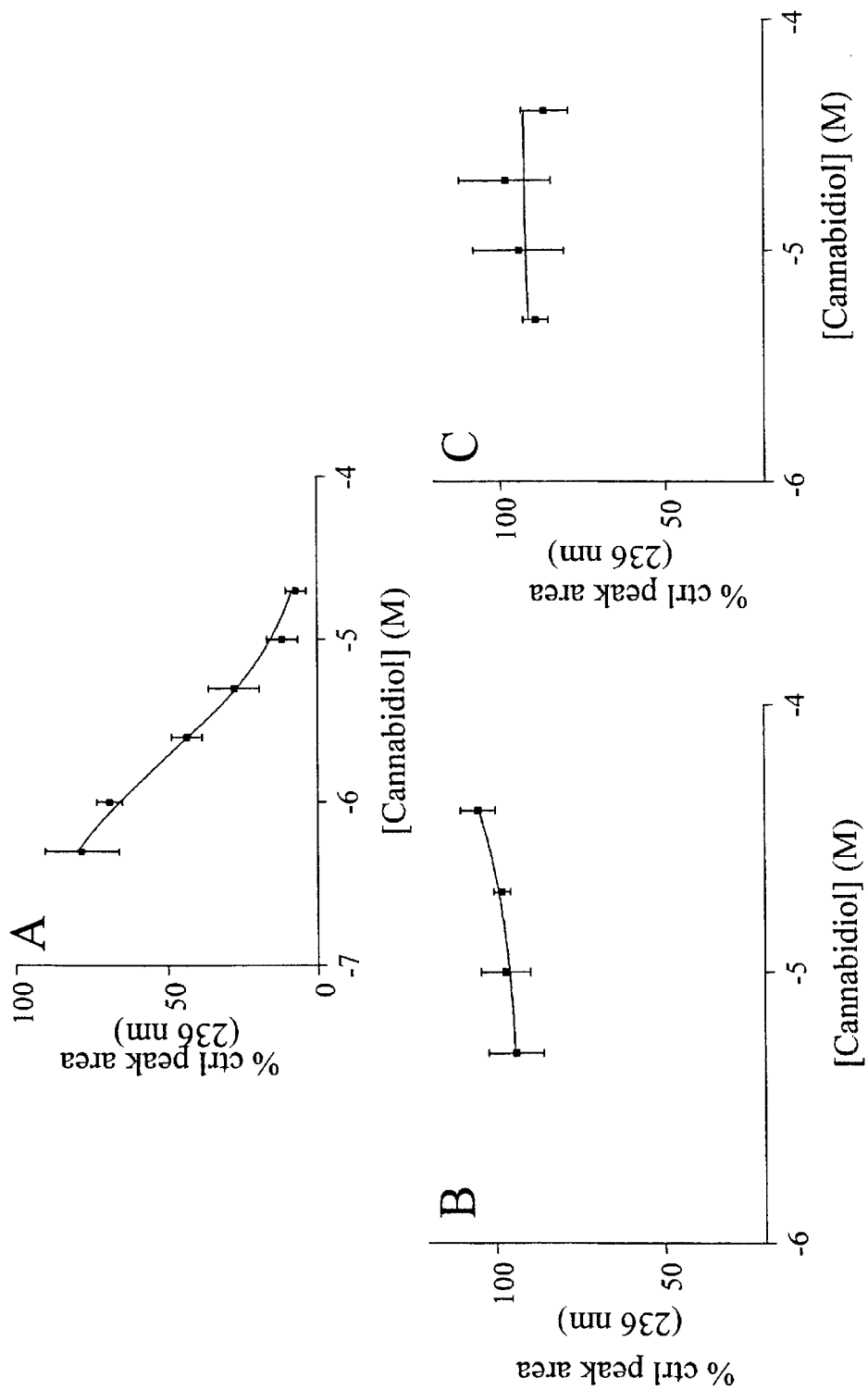
FIG. 7A is a graph similar to FIG. 6A, but was performed in whole cells rather than purified enzyme preparations, and shows the effect of CBD (as measured by the change in absorbance at 236 nm) on the enzymatic activity of 5-LO from cultured rat basophillic leukemia cells (RBL-2H3), which demonstrates that CBD inhibits 5-LO.
FIG. 7B is a graph showing the effect of CBD (as measured by the change in absorbance at 236 nm) on the formation of 12-HETE (the product of 12-LO) by human leukocytes (12-LO type 1).
FIG. 7C is a graph similar to FIG. 7B, showing the effect of CBD (as measured by the change in absorbance at 236 nm) on the formation of 12-HETE by human platelets (12-LO type 2).

Using whole cell preparations, the effect of CBD on 5- and 12-LO enzymes was investigated. As shown in FIG. 7A, CBD inhibited 5-LO in cultured rat basophillic leukemia cells (RBL-2H3) with an $EC_{50}$ of 1.92 µM. However, CBD had no effect on 12-LO, as monitored by the production of 12-HETE (the product of 12-LO), in either human leukocytes or platelets (FIGS. 7B and C). The leukocyte 12-LO is similar, while the platelet 12-LO is structurally and functionally different, from the porcine 12-LO used in the in vitro enzyme study.

Figure 8:
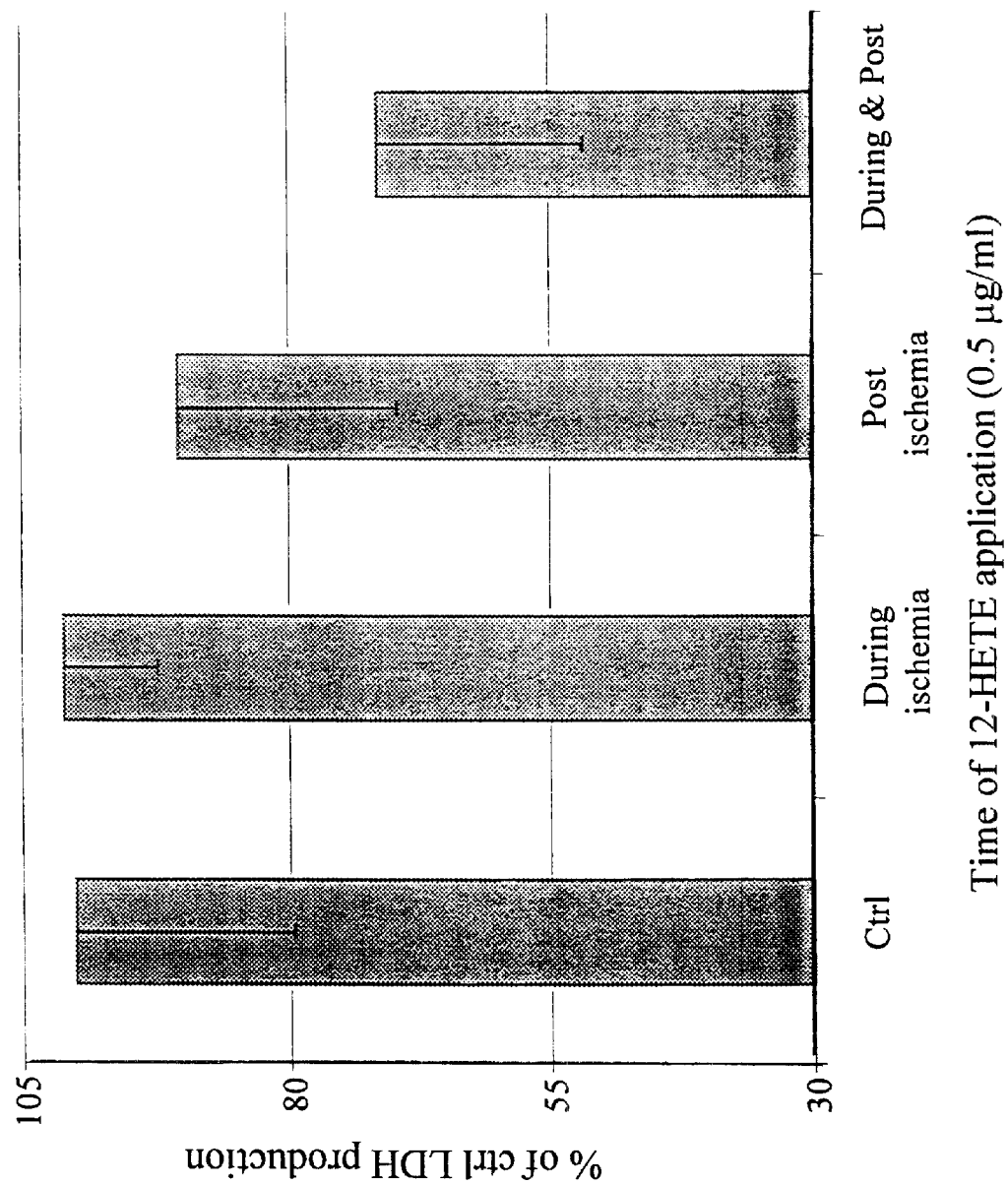
FIG. 8 is a bar graph demonstrating that 12-HETE can protect cortical neurons from NMDAr toxicity most effectively when administered during and post ischemia.

The ability of 12-HETE to protect cortical neurons from NMDAr toxicity is shown in FIG. 8. To achieve best protection from NMDAr toxicity, 12-HETE was administered both during and post ischemia.

Therefore, CBD serves as a selective inhibitor of at least two lipoxygenase enzymes, 5-LO and 15-LO, but had no effect on 12-LO. Importantly, this is the first demonstration (FIG. 8) that the 12-LO product 12-HETE can play a significant role in protecting neurons from NMDAr mediated toxicity. Although the mechanism of this protection is unknown at the present time, 12-HETE is known to be an important neuromodulator, due to its ability to influence potassium channel activity.

EXAMPLE 9

Methods of Treatment

The present invention includes a treatment that inhibits oxidation associated diseases in a subject such as an animal, for example a rat or human. The method includes administering the antioxidant drugs of the present invention, or a combination of the antioxidant drug and one or more other pharmaceutical agents, to the subject in a pharmaceutically compatible carrier and in an effective amount to inhibit the development or progression of oxidation associated diseases. Although the treatment can be used prophylactically in any patient in a demographic group at significant risk for such diseases, subjects can also be selected using more specific criteria, such as a definitive diagnosis of the condition. The administration of any exogenous antioxidant cannabinoid would inhibit the progression of the oxidation associated disease as compared to a subject to whom the cannabinoid was not administered. The antioxidant effect, however, increases with the dose of the cannabinoid.

The vehicle in which the drug is delivered can include pharmaceutically acceptable compositions of the drugs of the present invention using methods well known to those with skill in the art. Any of the common carriers, such as sterile saline or glucose solution, can be utilized with the drugs provided by the invention. Routes of administration include but are not limited to oral, intracranial ventricular (icv), intrathecal (it), intravenous (iv), parenteral, rectal, topical ophthalmic, subconjunctival, nasal, aural, sub-lingual (under the tongue) and transdermal. The antioxidant drugs of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like. Given the low solubility of many cannabinoids, they may be suspended in sesame oil.

Given the excellent absorption of the compounds of the present invention via an inhaled route, the compounds may also be administered as inhalants, for example in pharmaceutical aerosols utilizing solutions, suspensions, emulsions, powders and semisolid preparations of the type more fully described in Remington: The Science and Practice of Pharmacy ($19^{th}$ Edition, 1995) in chapter 95. A particular inhalant form is a metered dose inhalant containing the active ingredient, in a suspension or a dispersing agent (such as sorbitan trioleate, oleyl alcohol, oleic acid, or lecithin, and a propellant such as 12/11 or 12/114).

Embodiments of the invention comprising pharmaceutical compositions can be prepared with conventional pharmaceutically acceptable carriers, adjuvants and counterions as would be known to those of skill in the art. The compositions are preferably in the form of a unit dose in solid, semi-solid and liquid dosage forms such as tablets, pills, powders, liquid solutions or suspensions, injectable and infusible solutions, for example a unit dose vial, or a metered dose inhaler. Effective oral human dosage ranges for cannabidiol are contemplated to vary from about 1–40 mg/kg, for example 5–20 mg/kg, and in particular a dose of about 20 mg/kg of body weight.

If the antioxidant drugs are to be used in the prevention of cataracts, they may be administered in the form of eye drops formulated in a pharmaceutically inert, biologically acceptable carrier, such as isotonic saline or an ointment. Conventional preservatives, such as benzalkonium chloride, can also be added to the formulation. In ophthalmic ointments, the active ingredient is admixed with a suitable base, such as white petrolatum and mineral oil, along with antimicrobial preservatives. Specific methods of compounding these dosage forms, as well as appropriate pharmaceutical carriers, are known in the art. Remington: The Science and Practice of Pharmacy, 19th Ed., Mack Publishing Co. (1995), particularly Part 7.

The compounds of the present invention are ideally administered as soon as a diagnosis is made of an ischemic event, or other oxidative insult. For example, once a myocardial infarction has been confirmed by electrocardiograph, or an elevation in enzymes characteristic of cardiac injury (e.g. CKMB), a therapeutically effective amount of the cannabinoid drug is administered. A dose can also be given following symptoms characteristic of a stroke (motor or sensory abnormalities), or radiographic confirmation of a cerebral infarct in a distribution characteristic of a neurovascular thromboembolic event. The dose can be given by frequent bolus administration, or as a continuous IV dose. In the case of cannabidiol, for example, the drug could be given in a dose of 5 mg/kg active ingredient as a continuous intravenous infusion; or hourly intramuscular injections of that dose.

EXAMPLE 10

The following table lists examples of some dibenzopyran cannabinoids that may be useful as antioxidants in the method of the present invention.

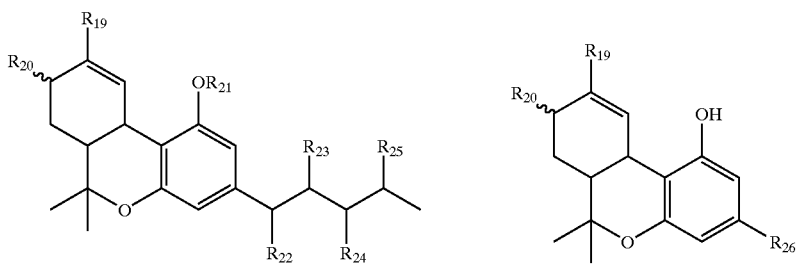

| | Compound | | $R_{19}$ | $R_{20}$ | $R_{21}$ | $R_{22}$ | $R_{23}$ | $R_{24}$ | $R_{25}$ | $R_{26}$ |
|---|---|---|---|---|---|---|---|---|---|---|
| H | 5 | 7-OH-$\Delta^1$-THC | $CH_2OH$ | H | H | H | H | H | H | $C_5H_{11}$ |
| H | 6 | 6α-OH-$\Delta^1$-THC | $CH_3$ | α-OH | | | | | | |
| H | 7 | 6β-OH-$\Delta^1$-THC | $CH_3$ | β-OH | | | | | | |
| | 8 | 1"-OH-$\Delta^1$-THC | $CH_3$ | | | OH | | | | |
| H | 9 | 2"-OH-$\Delta^1$-THC | $CH_3$ | | | | OH | | | |
| | 10 | 3"-OH-$\Delta^1$-THC | $CH_3$ | | | | | OH | | |
| | 11 | 4"-OH-$\Delta^1$-THC | $CH_3$ | | | | | | OH | |
| H | 12 | 6α,7-diOH-$\Delta^1$-THC | $CH_2OH$ | α-OH | | | | | | |
| H | 13 | 6v,7-diOH-$\Delta^1$-THC | $CH_2OH$ | β-OH | | | | | | |
| | 14 | 1",7-diOH-$\Delta^1$-THC | $CH_2OH$ | | | OH | | | | |
| H | 15 | 2",7-diOH-$\Delta^1$-THC | $CH_2OH$ | | | | OH | | | |
| H | 16 | 3",7-diOH-$\Delta^1$-THC | $CH_2OH$ | | | | | OH | | |
| H | 17 | 4",7-diOH-$\Delta^1$-THC | $CH_2OH$ | | | | | | OH | |
| | 18 | 1",6β-diOH-$\Delta^1$-THC | $CH_3$ | β-OH | | OH | | | | |
| | 19 | 1",3"-diOH-$\Delta^1$-THC | $CH_3$ | | | OH | | OH | | |
| | 20 | 1",6α,7-triOH-$\Delta^1$-THC | $CH_2OH$ | α-OH | | OH | | | | |
| H | 21 | $\Delta^1$-THC-6-one | $CH_3$ | =O | | | | | | |
| | 22 | Epoxyhexahydrocannabinol (EHHC)* | $CH_3$ | | | | | | | |
| | 23 | 7-oxo-$\Delta^1$-THC | CHO | | | | | | | |
| H | 24 | $\Delta^1$-THC-7"-oic acid | COOH | | | | | | | |
| H | 25 | $\Delta^1$-THC-3"-oic acid | $CH_3$ | | | | | | | $C_2H_4COOH$ |
| H | 26 | 1"-OH-$\Delta^1$-THC-7"-oic acid | COOH | | | OH | | | | |
| H | 27 | 2"-OH-$\Delta^1$-THC-7"-oic acid | COOH | | | | OH | | | |
| H | 28 | 3"-OH-$\Delta^1$-THC-7"-oic acid | COOH | | | | | OH | | |
| H | 29 | 4"-OH-$\Delta^1$-THC-7"-oic acid | COOH | | | | | | OH | |
| H | 30 | 3",4",5"-trisnor-2"-OH-$\Delta^1$-THC-7-oic acid | COOH | | | | | | | $C_2H_4OH$ |
| H | 31 | 7-OH-$\Delta^1$-THC-2"-oic acid | $CH_2OH$ | | | | | | | $CH_2COOH$ |
| H | 32 | 6β-OH-$\Delta^1$-THC-2"-oic acid | $CH_3$ | β-OH | | | | | | $CH_2COOH$ |
| H | 33 | 7-OH-$\Delta^1$-THC-3"-oic acid | $CH_2OH$ | | | | | | | $C_2H_4COOH$ |
| H | 34 | 6β-OH-$\Delta^1$-THC-3"-oic acid | $CH_3$ | β-OH | | | | | | $C_2H_4COOH$ |
| H | 35 | 6α-OH-$\Delta^1$-THC-4"-oic acid | $CH_3$ | α-OH | | | | | | $C_3H_6COOH$ |
| H | 36 | 2",3"-dehydro-6U-OH-$\Delta^1$-THC-4"-oic acid | $CH_3$ | α-OH | | | | | | $C_3H_4COOH$ |
| H | 37 | $\Delta^1$-THC-1",7-dioic acid | COOH | | | | | | | COOH |
| H | 38 | $\Delta^1$-THC-2",7-dioic acid | COOH | | | | | | | $CH_2COOH$ |
| H | 39 | $\Delta^1$-THC-3",7-dioic acid | COOH | | | | | | | $C_2H_4COOH$ |
| H | 40 | $\Delta^1$-THC-4",7-dioic acid | COOH | | | | | | | $C_3H_6COOH$ |
| H | 41 | 1",2"-dehydro-$\Delta^1$-THC-3",7-dioic acid | COOH | | | | | | | $C_2H_2COOH$ |
| H | 42 | $\Delta^1$-THC-glucuronic acid | $CH_3$ | | gluc† | | | | | |
| H | 43 | $\Delta^1$-THC-7-oic acid glucuronide | COO | gluc† | | | | | | |

*Epoxy group in C-1 and C-2 positions
†Glucuronide
Note: R-group substituents are H if not indicated otherwise.

Chemical structures of some of the dibenzopyran cannabinoids are shown below.

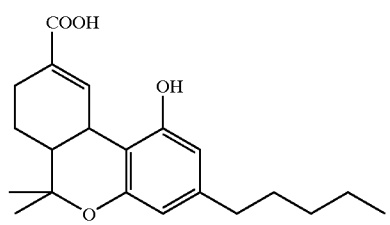

24

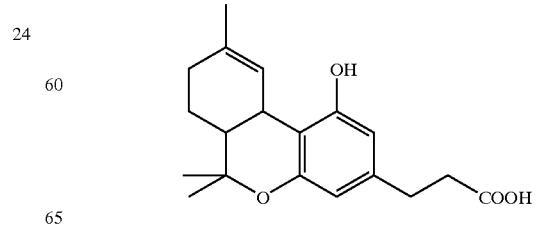

25

26
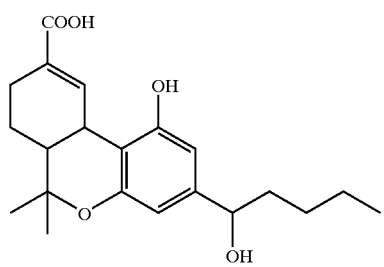
27
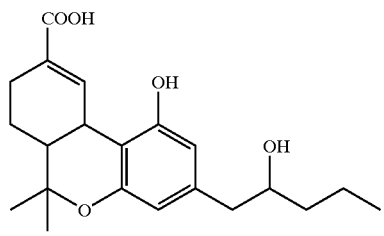
28
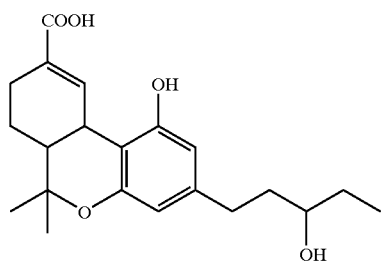
29
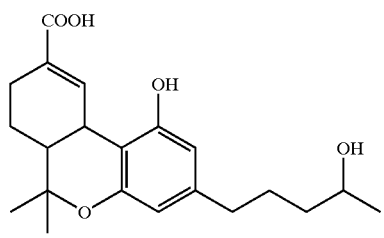
30
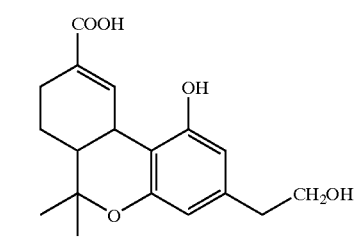
31
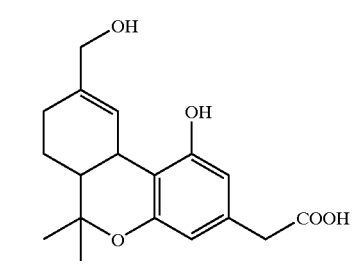
32
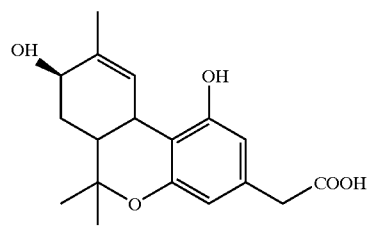
33
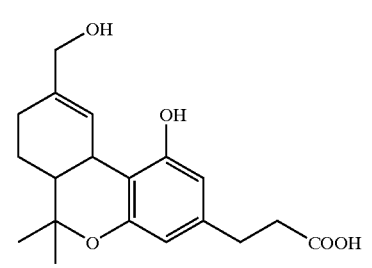
34
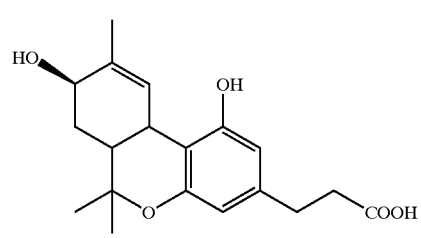
35
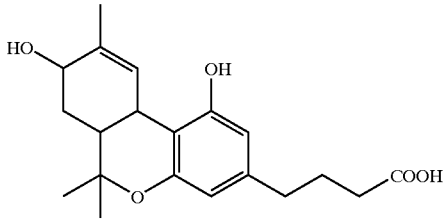
36
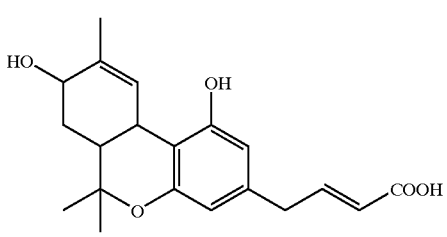
37
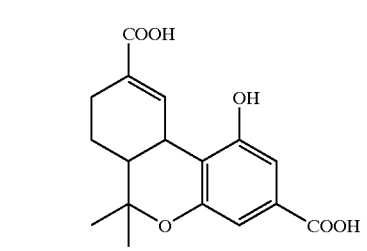

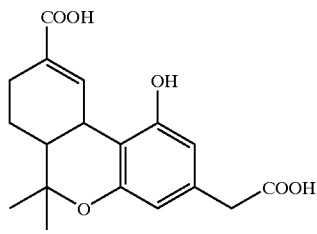

38

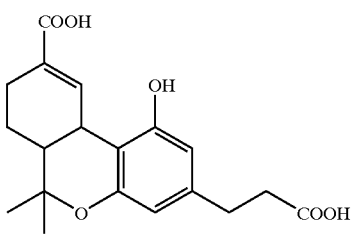

39

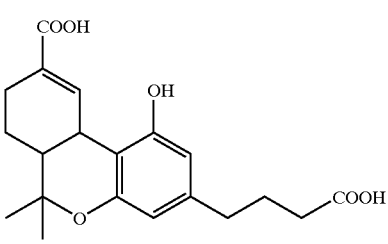

40

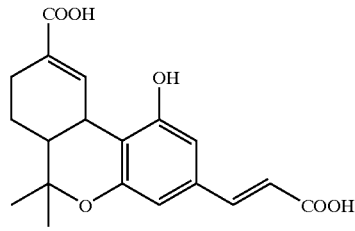

41

EXAMPLE 11

Examples of Structural Analogs of Cannabidiol

The following table lists examples of some cannabinoids which are structural analogs of cannabidiol and that may be useful as antioxidants in the method of the present invention. A particularly useful example is compound CBD, cannabidiol.

| Compound | $R_{19}$ | $R_{20}$ | $R_{21}$ | $R_{22}$ | $R_{23}$ | $R_{24}$ | $R_{25}$ | $R_{26}$ |
|---|---|---|---|---|---|---|---|---|
| 44 CBD | $CH_3$ | H | H | H | H | H | H | $C_5H_{11}$ |
| 45 7-OH—CBD | $CH_2OH$ | | | | | | | |
| 46 6α- | $CH_3$ | α-OH | | | | | | |
| 47 6β- | $CH_3$ | β-OH | | | | | | |
| 48 1"- | $CH_3$ | | | OH | | | | |
| 49 2"- | $CH_3$ | | | | OH | | | |
| 50 3"- | $CH_3$ | | | | | OH | | |
| 51 4"- | $CH_3$ | | | | | | OH | |
| 52 5"- | $CH_3$ | | | | | | | $C_4H_8CH_2OH$ |
| 53 6,7-diOH—CBD | $CH_2OH$ | OH | | | | | | |
| 54 3",7-diOH—CBD | $CH_2OH$ | | | | | OH | | |
| 55 4",7-diOH—CBD | $CH_2OH$ | | | | | | OH | |
| 56 CBD-7-oic acid | COOH | | | | | | | |
| 57 CBD-3"-oic acid | $CH_3$ | | | | | | | $C_2H_4COOH$ |

-continued

| Compound | $R_{19}$ | $R_{20}$ | $R_{21}$ | $R_{22}$ | $R_{23}$ | $R_{24}$ | $R_{25}$ | $R_{26}$ |
|---|---|---|---|---|---|---|---|---|
| 58 CBN | | | $CH_3$ | H | H | H | H | H | $C_5H_{11}$ |
| 59 7-OH—CBN | | | $CH_2OH$ | | | | | |
| 60 1"-OH—CBN | | | $CH_3$ | OH | | | | |
| 61 2"-OH—CBN | | | $CH_3$ | | OH | | | |
| 62 3"-OH—CBN | | | $CH_3$ | | | OH | | |
| 63 4"-OH—CBN | | | $CH_3$ | | | | OH | |
| 64 5"-OH—CBN | | | $CH_3$ | | | | | $C_4H_8CH_2OH$ |
| 65 2"-7-diOH—CBN | | | $CH_2OH$ | | OH | | | |
| 66 CBN-7-oic acid | | | COOH | | | | | |
| 67 CBN-1"-oic acid | | | $CH_3$ | COOH | | | | |
| 68 CBN-3"-oic acid | | | $CH_3$ | | | $C_2H_4COOH$ | | |

Note: R-group substituents are H if not indicated otherwise.

The invention being thus described, variation in the materials and methods for practicing the invention will be apparent to one of ordinary skill in the art. Such variations are to be considered within the scope of the invention, which is set forth in the claims below.

We claim:

1. A method of treating diseases caused by oxidative stress, comprising administering a therapeutically effective amount of a cannabinoid that has substantially no binding to the NMDA receptor to a subject who has a disease caused by oxidative stress.

2. The method of claim 1, wherein the cannabinoid is nonpsychoactive.

3. The method of claim 2, wherein the cannabinoid has a volume of distribution of 10 L/kg or more.

4. The method of claim 1, wherein the cannabinoid is not an antagonist at the NMDA receptor.

5. The method of claim 1, wherein the cannabinoid is:

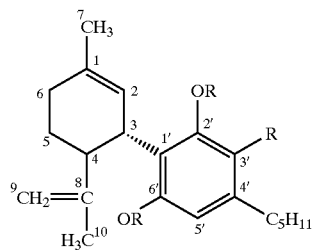

where R is H, substituted or unsubstituted alkyl, carboxyl, alkoxy, aryl, aryloxy, arylalkyl, halo or amino.

6. The method of claim 5, wherein R is H, substituted or unsubstituted alkyl, carboxyl or alkoxy.

7. The method of claim 2, wherein the cannabinoid is:

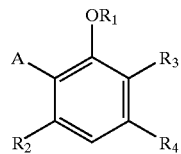

where

A is cyclohexyl, substituted or unsubstituted aryl, or

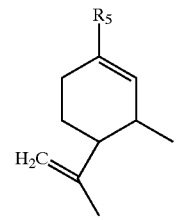

but not a pinene;

$R_1$ is H, substituted or unsubstituted alkyl, or substituted or unsubstituted carboxyl;

$R_2$ is H, lower substituted or unsubstituted alkyl, or alkoxy;

$R_3$ is of H, lower substituted or unsubstituted alkyl, or substituted or unsubstituted carboxyl;

$R_4$ is H, hydroxyl, or lower substituted or unsubstituted alkyl; and $R_5$ is H, hydroxyl, or lower substituted or unsubstituted alkyl.

8. The method of claim 7, wherein $R_1$ is lower alkyl, COOH or $COCH_3$;

$R_2$ is unsubstituted $C_1$–$C_5$ alkyl, hydroxyl, methoxy or ethoxy;

$R_3$ is H, unsubstituted $C_1$–$C_3$ alkyl, or $COCH_3$;

$R_4$ is hydroxyl, pentyl, heptyl, or diemthylheptyl; and $R_5$ is hydroxyl or methyl.

9. The method of claim 1, wherein the cannabinoid is:

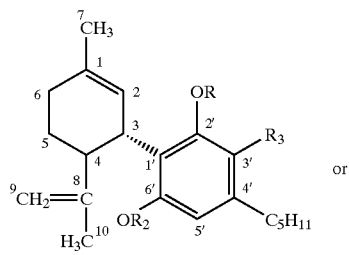

or

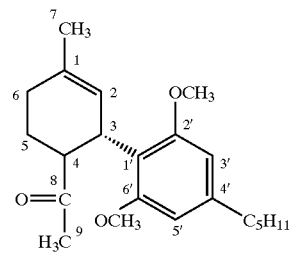

where $R_1$, $R_2$ and $R_3$ are independently H, $CH_3$, or $COCH_3$.

10. The method of claim 9, wherein the cannabinoid is:

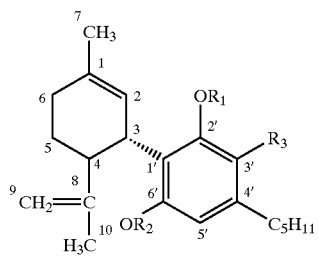

where:

a) $R_1=R_2=R_3=H$;

b) $R_1=R_3=H$, $R_2=CH_3$;

c) $R_1=R_2=CH_3$, $R_3=H$;

d) $R_1=R_2=COCH_3$, $R_3=H$; or e) $R_1=H$, $R_2=R_3=COCH_3$.

11. The method of claim 2, wherein the cannabinoid is:

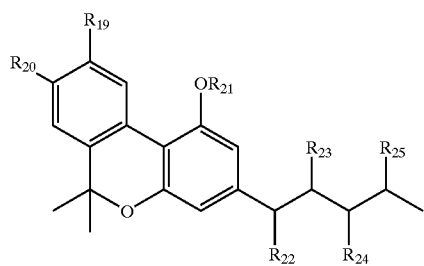

-continued

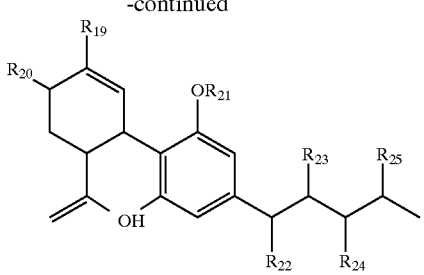

where $R_{19}$ is H, lower alkyl, lower alcohol, or carboxyl; $R_{20}$ is H or OH; and $R_{21}$–$R_{25}$ are independently H or OH.

12. The method of claim 11, wherein $R_{19}$ is H, $CH_3$, $CH_2OH$, or COOH, and $R_{20}$–$R_{24}$ are independently H or OH.

13. The method of claim 2, wherein the cannabinoid is:

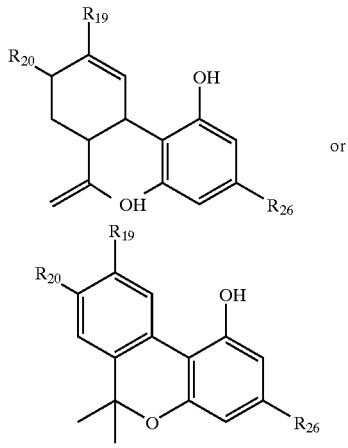

where $R_{19}$ and $R_{20}$ are H, and $R_{26}$ is alkyl.

14. The method of claim 10, wherein the cannabinoid is cannabidiol.

15. A method of treating an ischemic or neurodegenerative disease in the central nervous system of a subject, comprising administering to the subject a therapeutically effective amount of a cannabinoid, where the cannabinoid is

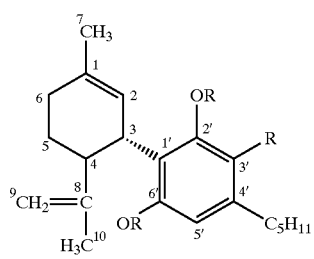

where R is H, substituted or unsubstituted alkyl, carboxyl, alkoxy, aryl, aryloxy, arylalkyl, halo or amino.

16. The method of claim 15, wherein the cannabinoid is not a psychoactive cannabinoid.

17. The method of claim 15 where the ischemic or neurodegenerative disease is an ischemic infarct, Alzheimer's disease, Parkinson's disease, and human immunodeficiency virus dementia, Down's syndrome, or heart disease.

18. A method of treating a disease with a cannabinoid that has substantially no binding to the NMDA receptor, comprising determining whether the disease is caused by oxidative stress, and if the disease is caused by oxidative stress, administering the cannabinoid in a therapeutically effective antioxidant amount.

19. The method of claim 18, wherein the cannabinoid has a volume of distribution of at least 1.5 L/kg and substantially no activity at the cannabinoid receptor.

20. The method of claim 19, wherein the cannabinoid has a volume of distribution of at least 10 L/kg.

21. The method of claim 1, wherein the cannabinoid selectively inhibits an enzyme activity of 5- and 15-lipoxygenase more than an enzyme activity of 12-lipoxygenase.

22. A method of treating a neurodegenerative or ischemic disease in the central nervous system of a subject, comprising administering to the subject a therapeutically effective amount of a compound selected from any of the compounds of claims 9 through 13.

23. The method of claim 22 where the compound is cannabidiol.

24. The method of claim 22, wherein the ischemic or neurodegenerative disease is an ischemic infarct, Alzheimer's disease, Parkinson's disease, and human immunodeficiency virus dementia, Down's syndrome, or heart disease.

25. The method of claim 24 wherein the disease is an ischemic infarct.

26. The method of claim 1, wherein the cannabinoid is not an antagonist at the AMPA receptor.

* * * * *

UNITED STATES PATENT AND TRADEMARK OFFICE
CERTIFICATE OF CORRECTION

PATENT NO. : 6,630,507 B1  Page 1 of 1
DATED : October 7, 2003
INVENTOR(S) : Hampson et al.

It is certified that error appears in the above-identified patent and that said Letters Patent is hereby corrected as shown below:

Column 13,
Line 23, "feral" should read -- fetal --.

Column 30,
Line 16, reads "$R_{20}$-$R_{24}$" should read -- $R_{20}$-$R_{25}$ --.

Signed and Sealed this

Fifteenth Day of June, 2004

JON W. DUDAS
*Acting Director of the United States Patent and Trademark Office*